(12) United States Patent
Dymock et al.

(10) Patent No.: US 6,518,293 B2
(45) Date of Patent: Feb. 11, 2003

(54) ANTI-HIV IMIDAZOLONE DERIVATIVES

(75) Inventors: Brian William Dymock, St. Albans (GB); Philip Stephen Jones, Welwyn Garden City (GB); John Herbert Merrett, Baldock (GB); Kevin Edward Burdon Parkes, Letchworth (GB); Martin John Parratt, Hertford (GB); Daryl Simon Walter, Knebworth (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/993,848

(22) Filed: Nov. 6, 2001

(65) Prior Publication Data

US 2002/0107272 A1 Aug. 8, 2002

(30) Foreign Application Priority Data

Nov. 22, 2000 (GB) .............................. 0028484

(51) Int. Cl.$^7$ ..................... C07D 401/06; A61K 31/415
(52) U.S. Cl. .................... 514/386; 514/392; 544/274.4; 548/314.7; 548/320.1
(58) Field of Search ....................... 546/274.4; 514/386, 514/392; 548/314.7, 320.1

(56) References Cited

U.S. PATENT DOCUMENTS 4,345,936 A * 8/1982 Thibault et al. ......... 548/320.1
5,612,636 A * 3/1997 Mohan et al. ............. 514/392

FOREIGN PATENT DOCUMENTS

| EP | 0 552 060 | 7/1993 |
| EP | 627 423 | 12/1994 |
| EP | 0 700 911 | 3/1996 |
| WO | WO 94/10168 | 5/1994 |
| WO | WO 94 10168 | 5/1994 |
| WO | WO 96/38421 | 12/1996 |
| WO | WO 00/35907 | * 6/2000 |

OTHER PUBLICATIONS

Reisch, Johannes, Chim. Ther., (5–6), pp. 335–336 (1996).
Cas Abstract, US 4345936, 08, 1982, Thibault et al.*
D.L. Comins et al., *Tetrahedron Letters*, vol. 27, pp. 1869–1872 (1986).
Pauwels et al., *J. Virology Methods*, vol. 20, pp. 309–321 (1988).

* cited by examiner

*Primary Examiner*—Joseph K. McKane
*Assistant Examiner*—Kamal Saeed
(74) *Attorney, Agent, or Firm*—George W. Johnston; Dennis P. Tramaloni

(57) ABSTRACT

The invention is concerned with novel imidazolone derivatives, a process for their manufacture, pharmaceutical compositions and the use of such compounds in medicine. In particular, the compounds are inhibitors of the human immunodeficiency virus reverse transcriptase enzyme which is involved in viral replication. Consequently the compounds of this invention may be advantageously used as therapeutic agents against HIV infection.

14 Claims, No Drawings

ANTI-HIV IMIDAZOLONE DERIVATIVES

BACKGROUND OF THE INVENTION

The present invention to compounds and methods for the treatment of infection by the human immunodeficiency virus (HIV). The disease Acquired Immune Deficiency Syndrome (AIDS) is the end result of infection by the distinct retroviruses, human immunodeficiency virus type-1 (HIV-1) or type-2 (HIV-2). Several critical points in the virus life cycle have been identified as possible targets for therapeutic intervention. Inhibition of one of these, the transcription of viral RNA to viral DNA (reverse transcriptase, RT), has provided a number of the current therapies used in treating AIDS. Inhibition of reverse transcriptase provided the first form of treatment for HIV infection with 3'-azido-3'-deoxythymidine (AZT). Since then several inhibitors have been launched, broadly forming two classes: nucleoside analogues and non-nucleosides. As an example of the latter it has been found that certain benzoxazinones, e.g. efavirenz are useful in the inhibition of HIV RT. However, development of strains of the virus resistant to current RT inhibitors is a constant problem. Therefore, development of compounds effective against resistant strains is an important goal.

Imidazolone derivatives have been described in the literature with different uses in the treatment of the human body.

WO 94/10168 describes imidazolone derivatives and their use as tachykinin receptor antagonists.

WO 96/38421 describes imidazolone derivatives and their use as anti-coagulants.

WO 00/35907 describes imidazolone derivatives and their use in treating benign prostatic hyperplasia.

SUMMARY OF THE INVENTION

The invention is concerned with novel imidazolone derivatives, a process for their manufacture, pharmaceutical compositions and the use of such compounds in medicine. In particular, the compounds are inhibitors of the human immunodeficiency virus reverse transcriptase enzyme which is involved in viral replication. Consequently the compounds of this invention may be advantageously used as therapeutic agents for the treatment of diseases caused by HIV infection.

DETAILED DESCRIPTION OF THE INVENTION

The present invention comprises compounds of formula I which are active against HIV:

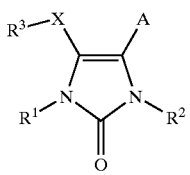

I wherein $R^1$ is hydrogen, alkyl, cycloalkyl, aryl or alkyl substituted with optionally substituted phenyl;

$R^2$ is hydrogen, alkenyl, alkyl or alkyl substituted with optionally substituted phenyl;

$R^3$ is alkyl, cycloalkyl, optionally substituted phenyl, optionally substituted benzyl or heterocyclyl;

A is alkyl, hydroxy-alkyl, alkenyl, substituted alkenyl, aryl-CH(OH)—, substituted alkyl, or A is a group of formula Z—$CH_2$—Y—$CH_2$—,
wherein Y is O or NR wherein R is hydrogen or alkyl and
Z is heterocyclyl or optionally substituted aryl;

X is S or O;

with the provisos that
(i) only one of $R^1$ and $R^2$ is hydrogen;
(ii) when X is O, then $R^1$ cannot be aryl;

as well as hydrolyzable esters or ethers of compounds of formula I and pharmaceutically acceptable salts thereof.

The term "alkyl" as used herein denotes an optionally substituted straight or branched chain hydrocarbon residue containing 1 to 12 carbon atoms, such as methyl, ethyl, n-propyl, isopropyl, n-butyl, sec-butyl, isobutyl, tert.-butyl, pentyl, hexyl, heptyl, octyl, nonyl, decyl, undecyl, dodecyl including their different isomers. Preferably, the term "alkyl" denotes an optionally substituted straight or branched chain hydrocarbon residue containing 1 to 7 carbon atoms.

Substituents for the alkyl chain are selected from one or more of aryl, heterocyclyl, alkoxy, hydroxy or halogen.

Aryl or heterocyclyl as substituents for the alkyl group are preferably substituted with 1, 2, 3, 4, 5 or where possible more methyl, ethyl, propyl, isopropyl, n-butyl, sec-butyl, isobutyl, tert.-butyl, methoxy, ethoxy, n-propyloxy, iso-propyloxy, n-butyloxy, iso-butyloxy, tert.-butyloxy, hydroxy, fluorine, chlorine, bromine or iodine.

Alkyl in $R^1$, $R^2$ and $R^3$ is preferably an optionally substituted straight or branched chain hydrocarbon residue containing 1 to 7 carbon atoms. Preferred substituents for such alkyl groups are selected from aryl, heterocyclyl, hydroxy or halogen. Preferred alkyl groups in $R^1$, $R^2$ and $R^3$ are unsubstituted straight or branched chain hydrocarbon residues containing 1 to 7 carbon atoms and more preferred alkyl groups in $R^1$, $R^2$ and $R^3$ are methyl, ethyl, propyl, isopropyl, n-butyl, sec-butyl, isobutyl, tert.-butyl or pentyl. Most preferred alkyl group in $R^1$, $R^2$ and $R^3$ are methyl, ethyl, propyl, isopropyl, n-butyl, sec-butyl, isobutyl, tert.-butyl.

Alkyl for $R^1$ is preferably isopropyl.

Alkyl for $R^2$ is preferably methyl.

Alkyl for the substituent A is as defined above, preferably a straight or branched chain hydrocarbon residue containing 1 to 7 carbon atoms. More preferred alkyl group for the substituent A are methyl, ethyl, propyl, isopropyl, n-butyl, sec-butyl, isobutyl, tert.-butyl or pentyl.

The term "alkoxy" as used herein denotes an optionally substituted straight or branched chain alkyl-oxy group wherein the "alkyl" portion is as defined above such as methoxy, ethoxy, n-propyloxy, iso-propyloxy, n-butyloxy, iso-butyloxy, tert.-butyloxy, pentyloxy, hexyloxy, heptyloxy including their different isomers. More preferred alkoxy groups within the invention are methoxy, ethoxy, n-propyloxy, iso-propyloxy, n-butyloxy, iso-butyloxy or tert.-butyloxy.

The term "$C_{1-4}$-alkyl substituted with $C_{1-4}$-alkoxy, $C_{1-4}$-alkyl-carbonyl-oxy- or heterocyclyl-oxy" as used herein denotes a $C_{1-4}$-alkyl, preferably $C_{1-2}$-alkyl as defined above which may be substituted with 1–3, preferably 1–2 and more preferably on substituents selected from $C_{1-4}$-alkoxy (preferred $C_{1-2}$-alkoxy), $C_{1-4}$-alkyl-carbonyl-oxy- (preferred $C_{1-2}$-alkyl-carbonyl-oxy-) and heterocyclyl-oxy. Preferred examples are methoxymethyl, ethoxymethyl, methyl-carbonyl-oxy-, ethyl-carbonyl-oxy-, 4-pyridyl-oxy-methyl, 3-pyridyl-oxy-methyl, 2-pyridyl-oxy-methyl.

The term "$C_{1-4}$-alkyl substituted with optionally substituted phenyl" as used herein denotes a $C_{1-4}$-alkyl, preferably $C_{1-2}$-alkyl as defined above which may be substituted with a phenyl group or with a substituted phenyl group which may be substituted with 1,2,3,4 or 5 substituents, preferably 1, 2 or 3 substituents selected from $C_{1-4}$-alkyl, $C_{1-4}$-alkoxy, hydroxy, fluorine, chlorine or bromine, preferably methyl, ethyl, methoxy, ethoxy, hydroxy, fluorine, chlorine or bromine. Examples are phenylmethyl (benzyl), phenylethyl, phenylpropyl, phenylbutyl, tolylmethyl, tolylethyl, tolylpropyl, tolylbutyl, 2,3-dimethylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl, 3,6-dimethylphenylmethyl, 2-methoxy-phenylmethyl, 3-methoxy-phenylmethyl, 4-methoxy-phenylmethyl, methoxy-phenylethyl, methoxy-phenylpropyl, methoxy-phenylbutyl, dimethoxy-phenylmethyl, dimethoxy-phenylethyl, dimethoxy-phenylpropyl, dimethoxy-phenylbutyl, 2-hydroxyphenylmethyl, 3-hydroxyphenylmethyl, 4-hydroxyphenylmethyl, 2,3-dihydroxyphenylmethyl, 2,4-dihydroxyphenylmethyl, 2,5-dihydroxyphenylmethyl, 2,6-dihydroxyphenylmethyl, 3,4-dihydroxyphenylmethyl, 3,5-dihydroxyphenylmethyl, 3,6-dihydroxyphenylmethyl, 2-hydroxyphenylethyl, 3- hydroxyphenylethyl, 4-hydroxyphenylethyl, 2-hydroxyphenylpropyl, 3-hydroxyphenylpropyl, 4-hydroxyphenylpropyl, 2-hydroxyphenylbutyl, 3-hydroxyphenylbutyl, 4-hydroxyphenylbutyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, 3,6-difluorophenylmethyl, 2- fluorophenylethyl, 3-fluorophenylethyl or 4-fluorophenylethyl, 2-chlorophenylmethyl, 3-chlorophenylmethyl, 4-chlorophenylmethyl, 2,3-dichlorophenylmethyl, 2,4-dichlorophenylmethyl, 2,5-dichlorophenylmethyl, 2,6-dichlorophenylmethyl, 3,4-dichlorophenylmethyl, 3,5-dichlorophenylmethyl, 3,6-dichlorophenylmethyl, 2-chlorophenylethyl, 3-chlorophenylethyl, 4-chlorophenylethyl, 2-bromophenylmethyl, 3-bromophenylmethyl, 4-bromophenylmethyl, 2,3-dibromophenylmethyl, 2,4-dibromophenylmethyl, 2,5-dibromophenylmethyl, 2,6-dibromophenylmethyl, 3,4-dibromophenylmethyl, 3,5-dibromophenylmethyl, 3,6-dibromophenylmethyl, 2-bromophenylethyl, 3-bromophenylethyl or 4-bromophenylethyl. In case more than one substituent is attached to the phenyl group, these substituents can be identical or different from each other and are also encompassed by the scope of the present invention. For example dimethoxy-phenylmethyl means that both methoxy substituents may be attached to the phenyl ring in the 2,3-position, the 2,4-position, the 2,5-position, the 2,6-position, the 3,4-position, the 3,5-position and the 3,6-position.

$C_{1-4}$-alkyl groups substituted with optionally substituted phenyl in $R^1$ are as defined above and preferably phenylmethyl (benzyl), phenylethyl, tolylmethyl, tolylethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl, 3,6-dimethylphenylmethyl, 2-methoxy-phenylmethyl, 3-methoxy-phenylmethyl, 4-methoxy-phenylmethyl, methoxy-phenylethyl, dimethoxy-phenylmethyl, dimethoxy-phenylethyl, 2-hydroxyphenylmethyl, 3-hydroxyphenylmethyl, 4-hydroxyphenylmethyl, 2,3-dihydroxyphenylmethyl, 2,4-dihydroxyphenylmethyl, 2,5-dihydroxyphenylmethyl, 2,6-dihydroxyphenylmethyl, 3,4-dihydroxyphenylmethyl, 3,5-dihydroxyphenylmethyl, 3,6-dihydroxyphenylmethyl, 2-hydroxyphenylethyl, 3-hydroxyphenylethyl, 4-hydroxyphenylethyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, 3,6-difluorophenylmethyl, 2-fluorophenylethyl, 3-fluorophenylethyl or 4-fluorophenylethyl, 2-chlorophenylmethyl, 3-chlorophenylmethyl, 4-chlorophenylmethyl, 2,3-dichlorophenylmethyl, 2,4-dichlorophenylmethyl, 2,5-dichlorophenylmethyl, 2,6-dichlorophenylmethyl, 3,4-dichlorophenylmethyl, 3,5-dichlorophenylmethyl, 3,6-dichlorophenylmethyl, 2-chlorophenylethyl, 3-chlorophenylethyl, 4-chlorophenylethyl, 2-bromophenylmethyl, 3-bromophenylmethyl, 4-bromophenylmethyl, 2,3-dibromophenylmethyl, 2,4-dibromophenylmethyl, 2,5-dibromophenylmethyl, 2,6-dibromophenylmethyl, 3,4-dibromophenylmethyl, 3,5-dibromophenylmethyl, 3,6-dibromophenylmethyl, 2-bromophenylethyl, 3-bromophenylethyl or 4-bromophenylethyl. Most preferred $C_{1-4}$-alkyl substituted with optionally substituted phenyl in $R^1$ are phenylmethyl (benzyl), phenylethyl, tolylmethyl, tolylethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl or 3,6-dimethylphenylmethyl.

$C_{1-4}$-alkyl groups substituted with optionally substituted phenyl in $R^2$ are as defined above and preferably phenylmethyl(benzyl), phenylethyl, tolylmethyl, tolylethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl, 3,6-dimethylphenylmethyl, 2-methoxy-phenylmethyl, 3-methoxy-phenylmethyl, 4-methoxy-phenylmethyl, methoxy-phenylethyl, dimethoxy-phenylmethyl, dimethoxy-phenylethyl, 2-hydroxyphenylmethyl, 3-hydroxyphenylmethyl, 4-hydroxyphenylmethyl, 2,3-dihydroxyphenylmethyl, 2,4-dihydroxyphenylmethyl, 2,5-dihydroxyphenylmethyl, 2,6-dihydroxyphenylmethyl, 3,4-dihydroxyphenylmethyl, 3,5-dihydroxyphenylmethyl, 3,6-dihydroxyphenylmethyl, 2-hydroxyphenylethyl, 3-hydroxyphenylethyl, 4-hydroxyphenylethyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, 3,6-difluorophenylmethyl, 2-fluorophenylethyl, 3-fluorophenylethyl or 4-fluorophenylethyl, 2-chlorophenylmethyl, 3-chlorophenylmethyl, 4-chlorophenylmethyl, 2,3-dichlorophenylmethyl, 2,4-dichlorophenylmethyl, 2,5-dichlorophenylmethyl, 2,6-dichlorophenylmethyl, 3,4-dichlorophenylmethyl, 3,5-dichlorophenylmethyl, 3,6-dichlorophenylmethyl, 2-chlorophenylethyl, 3-chlorophenylethyl, 4-chlorophenylethyl, 2-bromophenylmethyl, 3-bromophenylmethyl, 4-bromophenylmethyl, 2,3-dibromophenylmethyl, 2,4-dibromophenylmethyl, 2,5-dibromophenylmethyl, 2,6-dibromophenylmethyl, 3,4-dibromophenylmethyl, 3,5-dibromophenylmethyl, 3,6-dibromophenylmethyl, 2-bromophenylethyl, 3-bromophenylethyl or 4-bromophenylethyl. Most preferred $C_{1-4}$-alkyl substituted with optionally substituted phenyl in $R^2$ are phenylmethyl (benzyl), phenylethyl, tolylmethyl, tolylethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl, 3,6-dimethylphenylmethyl, methoxy-phenylmethyl, methoxy-phenylethyl, dimethoxy-phenylmethyl or dimethoxy-phenylethyl.

$C_{1-4}$-alkyl groups substituted with optionally substituted phenyl for the substituent A are as defined above, preferably phenylmethyl(benzyl), phenylethyl, tolylmethyl, tolylethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl, 3,6-dimethylphenylmethyl, 2-methoxy-phenylmethyl, 3-methoxy-phenylmethyl, 4-methoxy-phenylmethyl, methoxy-phenylethyl, dimethoxy-phenylmethyl, dimethoxy-phenylethyl, 2-hydroxyphenylmethyl, 3-hydroxyphenylmethyl, 4-hydroxyphenylmethyl, 2,3-dihydroxyphenylmethyl, 2,4-dihydroxyphenylmethyl, 2,5-dihydroxyphenylmethyl, 2,6-dihydroxyphenylmethyl, 3,4-dihydroxyphenylmethyl, 3,5-dihydroxyphenylmethyl, 3,6-dihydroxyphenylmethyl, 2-hydroxyphenylethyl, 3-hydroxyphenylethyl, 4-hydroxyphenylethyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, 3,6-difluorophenylmethyl, 2-fluorophenylethyl, 3-fluorophenylethyl or 4-fluorophenylethyl, 2-chlorophenylmethyl, 3-chlorophenylmethyl, 4-chlorophenylmethyl, 2,3-dichlorophenylmethyl, 2,4-dichlorophenylmethyl, 2,5-dichlorophenylmethyl, 2,6-dichlorophenylmethyl, 3,4-dichlorophenylmethyl, 3,5-dichlorophenylmethyl, 3,6-dichlorophenylmethyl, 2-chlorophenylethyl, 3-chlorophenylethyl, 4-chlorophenylethyl, 2-bromophenylmethyl, 3-bromophenylmethyl, 4-bromophenylmethyl, 2,3-dibromophenylmethyl, 2,4-dibromophenylmethyl, 2,5-dibromophenylmethyl, 2,6-dibromophenylmethyl, 3,4-dibromophenylmethyl, 3,5-dibromophenylmethyl, 3,6-dibromophenylmethyl, 2-bromophenylethyl, 3-bromophenylethyl or 4-bromophenylethyl. Most preferred $C_{1-4}$-alkyl substituted with optionally substituted phenyl for the substituent A are phenylmethyl(benzyl), phenylethyl, tolylmethyl, tolylethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl, 3,6-dimethylphenylmethyl, 2-hydroxyphenylmethyl, 3-hydroxyphenylmethyl, 4- hydroxyphenylmethyl, 2,3-dihydroxyphenylmethyl, 2,4-dihydroxyphenylmethyl, 2,5-dihydroxyphenylmethyl, 2,6-dihydroxyphenylmethyl, 3,4-dihydroxyphenylmethyl, 3,5-dihydroxyphenylmethyl, 3,6-dihydroxyphenylmethyl, 2-hydroxyphenylethyl, 3-hydroxyphenylethyl or 4-hydroxyphenylethyl.

The term "cycloalkyl" as used herein denotes an optionally substituted cycloalkyl group containing 3 to 8 carbon atoms, e.g. cyclopropyl, cyclobutyl, cyclopentyl, cyclohexyl, cycloheptyl or cyclooctyl.

Suitable substituents for cycloalkyl can be selected from those named for alkyl, in addition however an oxo group (=O) can be added to the selection.

Cycloalkyl in $R^1$ is as defined above and preferably cyclopropyl, cyclobutyl, cyclopentyl or cyclohexyl, preferably cyclopropyl or cyclobutyl and most preferred cyclopropyl. Cycloalkyl in $R^3$ is as defined above, preferably cyclopentyl, cyclohexyl or cycloheptyl and most preferred cyclohexyl.

The term "alkenyl" as used herein, and if not specified by the number of carbon atoms, denotes an unsubstituted or substituted hydrocarbon chain radical having from 2 to 8 carbon atoms, preferably from 2 to 4 carbon atoms, and having at least one olefinic double bond, including their different isomers. Examples are vinyl or allyl. A substituted alkenyl group as part of the invention can have the (E) or (Z) configuration. Both isomeric forms of these compounds are embraced by the present invention.

Suitable substituents for the alkenyl group can be selected from 1–2 (preferably 1) substituents selected from cyano, amino-carbonyl and $C_{1-4}$-alkyl-oxy-carbonyl. Alkenyl in $R^2$ is as defined above, preferably allyl.

Alkenyl for the substituent A is as defined above, preferably a vinyl group or a substituted vinyl group substituted with 1–2 (preferably 1) substituents selected from cyano, amino-carbonyl and $C_{1-4}$-alkyl-oxy-carbonyl. Examples are vinyl, acrylic acid ethyl ester, acrylonitrile, acrylamide. Both, the (E) or (Z) configuration are embraced by the present invention, however the (E) configuration is preferred.

The term "hydroxy-$C_{1-4}$-alkyl" as used herein denotes a $C_{1-4}$-alkyl, preferably a $C_{1-2}$-alkyl as defined above which is substituted with a hydroxy group. Examples are hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl.

The term "hydroxy-$C_{1-4}$-alkyl" for the substituent A is as defined above, preferably hydroxymethyl, 1-hydroxyethyl or 2-hydroxyethyl.

Formula "Z—$CH_2$—Y—$CH_2$—" as used herein denotes a chemical group wherein Y is O or NR wherein R is hydrogen or $C_{1-4}$-alkyl as defined above, preferably hydrogen; and Z is heterocyclyl or optionally substituted aryl with 1–3 benzyl-oxy groups (preferably 1–2 benzyl-oxy groups, more preferred 1 benzyl-oxy group). More preferred Z is aryl or heterocyclyl as defined below, preferably phenyl or 2-pyridyl, 3-pyridyl or 4-pyridyl.

Examples of the chemical group of formula "—$CH_2$—Y—$CH_2$—Z" are benzylaminomethyl, benzyloxymethyl, (pyridin-4-ylmethyl)aminomethyl, pyridin-4-ylmethoxymethyl, pyridin-3-ylmethoxymethyl, pyridin-4-ylmethoxymethyl or 4-benzyloxy-benzyloxymethyl.

The term "aryl" as used herein denotes an optionally substituted phenyl and naphthyl, both optionally benz-fused to an optionally substituted saturated, partially unsaturated or aromatic monocyclic, bicyclic or tricyclic heterocycle or carbocycle e.g. to cyclohexyl or cyclopentyl.

Substituents for aryl are selected from 1,2,3,4 or 5 of those named for alkyl as defined above and $C_{1-4}$-alkyl, $C_{1-4}$-alkoxy, hydroxy, fluorine, chlorine or bromine; they can be identical or different from each other. Preferred substituents for aryl are selected from $C_{1-4}$-alkyl, $C_{1-4}$-alkoxy, hydroxy, fluorine, chlorine or bromine.

In case more than one substituent is attached to the aryl group, these substituents can be identical or different from each other and are also encompassed by the scope of the present invention. For example dimethoxy-phenyl means that both methoxy substituents may be attached to the phenyl ring in the 2,3-position, the 2,4-position, the 2,5-position, the 2,6-position, the 3,4-position, the 3,5-position and the 3,6-position.

Examples of aryl groups are phenyl, 2-methyl-phenyl, 3-methyl-phenyl, 4-methyl-phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,6-dimethylphenyl, 2-methoxy-phenyl, 3-methoxy-phenyl, 4-methoxy-phenyl, 2,3-dimethoxy-phenyl, 2,4-dimethoxyphenyl, 2,5-dimethoxy-phenyl, 2,6-dimethoxy-phenyl, 3,4-dimethoxy-phenyl, 3,5-dimethoxy-phenyl, 3,6-dimethoxyphenyl, 2-hydroxyphenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxyphenyl, 3,5-dihydroxyphenyl, 3,6-dihydroxyphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 3,6-difluorophenyl 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 3,6-dichlorophenyl, 2-bromophenyl, 3-bromophenyl, 4-bromophenyl, 2,3-dibromophenyl, 2,4-dibromophenyl, 2,5-dibromophenyl, 2,6-dibromophenyl, 3,4-dibromophenyl, 3,5-dibromophenyl or 3,6-dibromophenyl.

Aryl in $R^1$ is as defined above and preferably phenyl, 2-methyl-phenyl, 3-methyl-phenyl, 4-methyl-phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,6-dimethylphenyl, 2-chloro-phenyl, 3-chloro-phenyl, 4-chloro-phenyl and most preferably phenyl.

Aryl in the formula "Z—$CH_2$—Y—$CH_2$—" as used herein denotes preferably one of the following groups: phenyl, 2-methyl-phenyl, 3-methyl-phenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,6-dimethylphenyl, 2-chloro-phenyl, 3-chloro-phenyl, 4-chloro-phenyl and most preferably phenyl.

The term "optionally substituted phenyl" in $R^3$ as used herein denotes a phenyl group which may be substituted with 1,2,3,4 or 5 substituents, preferred 1, 2 or 3 substituents, more preferred 1 or 2 substituents selected from $C_{1-4}$-alkyl, $C_{1-4}$-alkoxy, hydroxy, fluorine, chlorine, bromine and cyano or selected from $C_{1-4}$-alkyl, $C_{1-4}$-alkoxy, hydroxy, fluorine, chlorine or bromine, preferably methyl, ethyl, methoxy, ethoxy, hydroxy, fluorine, chlorine, bromine; or preferably methyl, ethyl, methoxy, ethoxy, hydroxy, fluorine, chlorine, bromine and cyano. Further preferred embodiments for "optionally substituted phenyl" in $R^3$ are 2-substituted phenyl rings and the more preferred 3-substituted phenyl rings. An especially preferred embodiment for "optionally substituted phenyl" in $R^3$ are 3,5-disubstituted phenyl rings.

Preferred examples are phenyl, 2-methyl-phenyl, 3-methyl-phenyl, 4-methyl-phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,6-dimethylphenyl, 2-methoxy-phenyl, 3-methoxy-phenyl, 4-methoxy-phenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,6-dimethoxyphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 3,6-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 3,6-dichlorophenyl, 2-bromophenyl, 3-bromophenyl, 4-bromophenyl, 2,3-dibromophenyl, 2,4-dibromophenyl, 2,5-dibromophenyl, 2,6-dibromophenyl, 3,4-dibromophenyl, 3,5-dibromophenyl, 3,6-dibromophenyl, 2-cyano-phenyl, 3-cyano-phenyl, 4-cyanophenyl, 2,3-dicyanophenyl, 2,4-dicyanophenyl, 2,5-dicyanophenyl, 2,6-dicyanophenyl, 3,4-dicyanophenyl, 3,5-dicyanophenyl or 3,6-dicyanophenyl. Most preferred optionally substituted phenyl in $R^3$ are phenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 3,6-dichlorophenyl.

The term "optionally substituted benzyl" in $R^3$ as used herein denotes a benzyl group which may be substituted with 1,2,3,4 or 5 substituents, preferably 1, 2 or 3 substituents selected from $C_{1-4}$-alkyl, $C_{1-4}$-alkoxy, hydroxy, fluorine, chlorine, bromine and cyano or selected from $C_{1-4}$-alkyl, $C_{1-4}$-alkoxy, hydroxy, fluorine, chlorine or bromine, preferably methyl, ethyl, methoxy, ethoxy, hydroxy, fluorine, chlorine or bromine. Preferred examples are benzyl, 2-methyl-benzyl, 3-methyl-benzyl, 4-methylbenzyl, 2,3-dimethylbenzyl, 2,4-dimethylbenzyl, 2,5-dimethylbenzyl, 2,6-dimethylbenzyl, 3,4-dimethylbenzyl, 3,5-dimethylbenzyl, 3,6-dimethylbenzyl, 2-methoxybenzyl, 3-methoxy-benzyl, 4-methoxy-benzyl, 2,3-dimethoxybenzyl, 2,4-dimethoxybenzyl, 2,5-dimethoxybenzyl, 2,6-dimethoxybenzyl, 3,4-dimethoxybenzyl, 3,5-dimethoxybenzyl, 3,6-dimethoxybenzyl, 2-hydroxy-benzyl, 3-hydroxy-benzyl, 4-hydroxy-benzyl, 2,3-dihydroxybenzyl, 2,4-dihydroxybenzyl, 2,5-dihydroxybenzyl, 2,6-dihydroxybenzyl, 3,4-dihydroxybenzyl, 3,5-dihydroxybenzyl, 3,6-dihydroxybenzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 3,6-difluorobenzyl, 2-chlorobenzyl, 3-chlorobenzyl, 4-chlorobenzyl, 2,3-dichlorobenzyl, 2,4-dichlorobenzyl, 2,5-dichlorobenzyl, 2,6-dichlorobenzyl, 3,4-dichlorobenzyl, 3,5-dichlorobenzyl, 3,6-dichlorobenzyl, 2-bromobenzyl, 3-bromobenzyl, 4-bromobenzyl, 2,3-dibromobenzyl, 2,4-dibromobenzyl, 2,5-dibromobenzyl, 2,6-dibromobenzyl, 3,4-dibromobenzyl, 3,5-dibromobenzyl 3,6-dibromobenzyl, 2-cyano-benzyl, 3-cyano-benzyl, 4-cyano-benzyl, 2,3-dicyanobenzyl, 2,4-dicyanobenzyl, 2,5-dicyanobenzyl, 2,6-dicyanobenzyl, 3,4-dicyanobenzyl, 3,5-dicyanobenzyl or 3,6-dicyanobenzyl. More preferred optionally substituted benzyl in $R^3$ is benzyl, 2-chlorobenzyl, 3-chlorobenzyl, 4-chlorobenzyl, 2,3-dichlorobenzyl, 2,4-dichlorobenzyl, 2,5-dichlorobenzyl, 2,6-dichlorobenzyl, 3,4-dichlorobenzyl, 3,5-dichlorobenzyl, 3,6-dichlorobenzyl and most preferably benzyl is the unsubstituted benzyl group.

In case more than one substituent is attached to the benzyl group, these substituents can be identical or different from each other and are also encompassed by the scope of the present invention. For example dimethoxy-benzyl means that both methoxy substituents may be attached to the phenyl ring in the 2,3-position, the 2,4-position, the 2,5-position, the 2,6-position, the 3,4-position, the 3,5-position and the 3,6-position.

The term "aryl-CH(OH)—" as used herein denotes a hydroxymethyl group which is substituted with an aryl group as defined above. A preferred aryl group is the phenyl group.

The term "heterocyclyl" as used herein denotes optionally substituted aromatic or non-aromatic monocyclic or bicyclic heterocyclic systems which contains one or more hetero atoms selected from nitrogen, oxygen and sulfur, such as furyl, 1-pyrrolyl, 2-pyrrolyl, 2-pyridyl, 3-pyridyl, 4-pyridyl, 1-indolyl, 2-indolyl or 3-indolyl.

Substituents for heterocyclyl are selected from 1,2,3,4 or 5 of those named for alkyl as defined above and $C_{1-4}$-alkyl, $C_{1-4}$-alkoxy, hydroxy, fluorine, chlorine or bromine; they can be identical or different from each other. Preferred substituents for heterocyclyl are selected from $C_{1-4}$-alkyl, $C_{1-4}$-alkoxy, hydroxy, fluorine, chlorine or bromine.

In case more than one substituent is attached to the heterocyclyl group, these substituents can be identical or different from each other and are also encompassed by the scope of the present invention. For example dimethylpyridyl means that both methyl substituents may be attached to the pyridyl in the chemically possible positions. For example both methyl substituents may be attached to the 2-pyridyl in the 3,4-position, the 4,5-position, the 5,6-position, the 3,5-position, the 3,6-position, the and the 4,6-position. Both methyl substituents may be attached to the 3-pyridyl in the 2,4-position, the 2,5-position, the 2,6-position, the 4,5-position, the 4,6-position, the and the 5,6-position. Both methyl substituents may be attached to the 4-pyridyl in the 2,3-position, the 2,5-position, the 2,6-position, and the 3,5-position.

Examples for "substituted heterocyclyl" are furyl, methylfuryl, dimethylfuryl, ethylfuryl, methoxyfuryl, dimethoxyfuryl, hydroxyfuryl, dihydroxyfuryl, fluorofuryl, difluorofuryl, chlorofuryl, dichlorofuryl, bromofuryl, dibromofuryl, pyrrolyl, methylpyrrolyl, dimethylpyrrolyl, ethylpyrrolyl, methoxypyrrolyl, dimethoxypyrrolyl, hydroxypyrrolyl, dihydroxypyrrolyl, fluoropyrrolyl, difluoropyrrolyl, chloropyrrolyl, dichloropyrrolyl, bromopyrrolyl, dibromopyrrolyl, pyridyl, methylpyridyl, dimethylpyridyl, ethylpyridyl, methoxypyridyl, dimethoxypyridyl, hydroxypyridyl, dihydroxypyridyl, fluoropyridyl, difluoropyridyl, chloropyridyl, dichloropyridyl, bromopyridyl, dibromopyridyl, indolyl, methylindolyl, dimethylindolyl, ethylindolyl, methoxyindolyl, dimethoxyindolyl, hydroxyindolyl, dihydroxyindolyl, fluoroindolyl, difluoroindolyl, chloroindolyl, dichloroindolyl, bromoindolyl or dibromoindolyl. For all the cited examples for "heterocyclyl" these substituents can be at any chemically possible position. For example methylpyridyl means that the methyl substituent may be attached in the 3, 4, 5 or 6 position of a 2-pyridyl or in the 2, 4, 5 or 6 position of a 3-pyridyl or in the 2, 3, 5 or 6 position of a 4-pyridyl.

Heterocyclyl in the formula "Z—$CH_2$—Y—$CH_2$—" as used herein denoted preferably one of the following groups as defined above, preferably unsubstituted furyl, 1-pyrrolyl, 2-pyrrolyl, 2-pyridyl, 3-pyridyl, 4-pyridyl, 1-indolyl, 2-indolyl or 3-indolyl and most preferably 2-pyridyl, 3-pyridyl or 4-pyridyl.

Heterocyclyl in $R^3$ is as defined above and preferably unsubstituted furyl, 1-pyrrolyl, 2-pyrrolyl, 2-pyridyl, 3-pyridyl, 4-pyridyl, 1-indolyl, 2-indolyl or 3-indolyl. More preferably heterocyclyl in $R^3$ is 2-pyridyl, 3-pyridyl or 4-pyridyl and most preferred 4-pyridyl. The term "$C_{1-4}$-alkyl substituted with optionally substituted heterocyclyl" as used herein denotes a $C_{1-4}$-alkyl, preferably $C_{1-2}$-alkyl group as defined above which may be substituted with an optionally substituted heterocyclyl group, preferably with an optionally substituted pyridyl group as defined above which may be substituted with 1,2,3 or 4 substituents, preferably 1 or 2 substituents selected from $C_{1-4}$-alkyl, $C_{1-4}$-alkoxy, hydroxy, fluorine, chlorine or bromine, preferably methyl, ethyl, methoxy, ethoxy, hydroxy, fluorine, chlorine or bromine. Examples are furylmethyl, furylethyl, furylpropyl, furylbutyl, methylfurylmethyl, methylfurylethyl, dimethylfurylmethyl, ethylfurylmethyl, methoxyfurylmethyl, methoxyfurylethyl, dimethoxyfurylmethyl, hydroxyfurylmethyl, hydroxyfurylethyl, dihydroxyfurylmethyl, fluorofurylmethyl, difluorofurylmethyl, chlorofurylmethyl, chlorofurylethyl, dichlorofurylmethyl, dichlorofurylmethyl, bromofurylmethyl, dibromofurylmethyl, pyrrolylmethyl, pyrrolylethyl, pyrrolylpropyl, pyrrolylbutyl, methylpyrrolylmethyl, methylpyrrolylethyl, dimethylpyrrolylmethyl, ethylpyrrolylmethyl, methoxypyrrolylmethyl, methoxypyrrolylethyl, dimethoxypyrrolylmethyl, hydroxypyrrolylmethyl, hydroxypyrrolylethyl, dihydroxypyrrolylmethyl, fluoropyrrolylmethyl, difluoropyrrolylmethyl, chloropyrrolylmethyl, chloropyrrolylethyl, dichloropyrrolylmethyl, dichloropyrrolylmethyl, bromopyrrolylmethyl, dibromopyrrolylmethyl, pyridylmethyl (more specific examples are 2-pyridylmethyl, 3-pyridylmethyl, 4-pyridylmethyl), pyridylethyl, pyridylpropyl, pyridylbutyl, methylpyridylmethyl, methylpyridylethyl, dimethylpyridylmethyl, ethylpyridylmethyl, methoxypyridylmethyl, methoxypyridylethyl, dimethoxypyridylmethyl, hydroxypyridylmethyl, hydroxypyridylethyl, dihydroxypyridylmethyl, fluoropyridylmethyl, difluoropyridylmethyl, chloropyridylmethyl, chloropyridylethyl, dichloropyridylmethyl, dichloropyridylmethyl, bromopyridylmethyl, dibromopyridylmethyl, indolylmethyl, indolylethyl, indolylpropyl, indolylbutyl, methylindolylmethyl, methylindolylethyl, dimethylindolylmethyl, ethylindolylmethyl, methoxyindolylmethyl, methoxyindolylethyl, dimethoxyindolylmethyl, hydroxyindolylmethyl, hydroxyindolylethyl, dihydroxyindolylmethyl, fluoroindolylmethyl, difluoroindolylmethyl, chloroindolylmethyl, chloroindolylethyl, dichloroindolylmethyl, dichloroindolylmethyl, bromoindolylmethyl or dibromoindolylmethyl.

For all the cited examples for "heterocyclyl" these substituents can be at any chemically possible position. For example methylpyridyl means that the methyl substituent may be attached in the 3, 4, 5 or 6 position of a 2-pyridyl or in the 2, 4, 5 or 6 position of a 3-pyridyl or in the 2, 3, 5 or 6 position of a 4-pyridyl.

The term "X" represents S and O, preferably S.

The term halogen stands for fluorine, chlorine, bromine and iodine.

Any functional (i.e. reactive) group present in a side-chain may be protected, with the protecting group being a group which is known per se, for example, as described in "Protective Groups in Organic Synthesis", 2nd Ed., T. W. Greene and P. G. M. Wuts, John Wiley & Sons, New York, N.Y., 1991. For example, an amino group can be protected by tert.-butoxycarbonyl (BOC) or benzyloxycarbonyl (Z).

The compounds of this invention may contain one or more asymmetric carbon atoms and may therefore occur as racemates and racemic mixtures, single enantiomers, diastereomeric mixtures and individual diastereomers. Furthermore, where a compound of the invention contains an olefinic double bond, this can have the (E) or (Z) configuration. Also, each chiral center may be of the R or S configuration. All such isomeric forms of these compounds are embraced by the present invention.

Compounds of formula I which are acidic can form pharmaceutically acceptable salts with bases such as alkali metal hydroxides, e.g. sodium hydroxide and potassium hydroxide; alkaline earth metal hydroxides, e.g. calcium hydroxide, barium hydroxide and magnesium hydroxide, and the like; with organic bases e.g. N-ethyl piperidine, dibenzylamine, and the like. Those compounds of formula (I) which are basic can form pharmaceutically acceptable salts with inorganic acids, e.g. with hydrohalic acids such as hydrochloric acid and hydrobromic acid, sulphuric acid, nitric acid and phosphoric acid, and the like, and with organic acids, e.g. with acetic acid, tartaric acid, succinic acid, fumaric acid, maleic acid, malic acid, salicylic acid, citric acid, methanesulphonic acid and p-toluene sulphonic acid, and the like. The formation and isolation of such salts can be carried out according to methods known in the art.

Preferred embodiments of the invention are compounds of formula I wherein $R^1$ is hydrogen, $C_{1-12}$-alkyl, $C_{3-8}$-cycloalkyl, aryl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine, preferred wherein $R^1$ is $C_{1-2}$-alkyl, aryl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine, more preferred wherein $R^1$ is $C_{1-7}$-alkyl, phenyl or $C_{1-4}$-alkyl substituted with phenyl, most preferred wherein $R^1$ is $C_{1-7}$-alkyl or $C_{1-4}$-alkyl substituted with phenyl;

$R^2$ is hydrogen, $C_{2-4}$-alkenyl, $C_{1-12}$-alkyl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine preferred wherein $R^2$ is $C_{2-4}$-alkenyl, $C_{1-12}$-alkyl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine,bromine, more preferred wherein $R^2$ is $C_{2-4}$-alkenyl, $C_{1-7}$-alkyl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine, most preferred wherein $R^3$ is $C_{2-4}$-alkenyl, $C_{1-7}$-alkyl or $C_{1-4}$-alkyl substituted with phenyl;

$R^3$ is $C_{1-12}$-alkyl, $C_{3-8}$-cycloalkyl, phenyl, benzyl or heterocyclyl, wherein a phenyl ring may be substituted with 1–5 substituents selected from $C_{1-4}$-alkyl, $C_{1-4}$-alkoxy, hydroxy, fluorine, chlorine, bromine and cyano, preferred wherein $R^3$ is $C_{1-12}$-alkyl, $C_{3-8}$-cycloalkyl, phenyl, benzyl or heterocyclyl, wherein a phenyl ring may be substituted with 1–5 substituents selected from $C_{1-4}$-alkyl, $C_{1-4}$-alkoxy, hydroxy, fluorine, chlorine, bromine and cyano, more preferred wherein $R^3$ is $C_{1-7}$-alkyl, $C_{3-6}$-cycloalkyl, phenyl, benzyl or heterocyclyl, wherein a phenyl ring may be substituted with 1–5 substituents selected from $C_{1-4}$-alkyl, $C_{1-4}$-alkoxy, hydroxy, fluorine, chlorine, bromine and cyano, most preferred wherein $R^3$ is $C_{1-4}$-alkyl, $C_{3-6}$-cycloalkyl or optionally substituted phenyl, wherein phenyl may be substituted with 1–5 substituents selected from $C_{1-4}$-alkyl, $C_{1-4}$-alkoxy, hydroxy, fluorine, chlorine, bromine and cyano;

A is $C_{1-12}$-alkyl, hydroxy-$C_{1-4}$-alkyl, $C_{2-4}$-alkenyl, substituted $C_{2-4}$-alkenyl, aryl-CH(OH)—, $C_{1-4}$-alkyl substituted with $C_{1-4}$-alkoxy, $C_{1-4}$-alkyl-carbonyl-oxy-, heterocyclyl-oxy or A is $C_{1-4}$-alkyl substituted with phenyl optionally substituted with 1–5 substituents or with heterocyclyl optionally substituted with 1–4 substituents selected from $C_{1-4}$-alkyl, $C_{1-4}$-alkoxy, hydroxy, fluorine, chlorine and bromine, wherein substituted $C_{2-4}$-alkenyl is substituted with 1–2 substituents selected from cyano, amino-carbonyl and $C_{1-4}$-alkyl-oxy-carbonyl, or A is a group of formula Z—$CH_2$—Y—$CH_2$—, wherein Y is O or NR wherein R is hydrogen or $C_{1-4}$-alkyl and Z is heterocyclyl or optionally substituted aryl with 1–3 benzyl-oxy groups, preferred wherein A is $C_{1-7}$-alkyl, hydroxy-$C_{1-4}$-alkyl, $C_{2-4}$-alkenyl, substituted $C_{2-4}$-alkenyl, aryl-CH(OH)—, $C_{1-4}$-alkyl substituted with $C_{1-4}$-alkoxy, $C_{1-4}$-alkyl-carbonyl-oxy-, heterocyclyl-oxy or A is $C_{1-4}$-alkyl substituted with phenyl optionally substituted with 1–5 substituents or with heterocyclyl optionally substituted with 1–4 substituents selected from $C_{1-4}$-alkyl, $C_{1-4}$-alkoxy, hydroxy, fluorine, chlorine and bromine, wherein substituted $C_{2-4}$-alkenyl is substituted with 1–2 substituents selected from cyano, amino-carbonyl and $C_{1-4}$-alkyl-oxy-carbonyl, or A is a group of formula Z—$CH_2$—Y—$CH_2$—, wherein Y is O or NR wherein R is hydrogen or $C_{1-4}$-alkyl and Z is heterocyclyl or optionally substituted aryl with 1–3 benzyl-oxy groups, more preferred wherein A is $C_{1-7}$-alkyl, hydroxy-$C_{1-4}$-alkyl, $C_{2-4}$-alkenyl, substituted $C_{2-4}$-alkenyl, phenyl-CH(OH)—, $C_{1-4}$-alkyl substituted with $C_{1-4}$-alkoxy, $C_{1-4}$-alkyl-carbonyl-oxy-, heterocyclyl-oxy or A is $C_{1-4}$-alkyl substituted with phenyl optionally substituted with 1–5 substituents or with pyridyl optionally substituted with 1–4 substituents selected from $C_{1-4}$-alkyl, $C_{1-4}$-alkoxy, hydroxy, fluorine, chlorine and bromine, wherein substituted $C_{2-4}$-alkenyl is substituted with 1–2 substituents selected from cyano, amino-carbonyl and $C_{1-4}$-alkyl-oxy-carbonyl, or A is a group of formula Z—$CH_2$—Y—$CH_2$—, wherein Y is O or NR wherein R is hydrogen or $C_{1-4}$-alkyl and Z is pyridyl or optionally substituted phenyl with 1–3 benzyl-oxy groups, most preferred wherein A is $C_{1-7}$-alkyl, $C_{2-4}$-alkenyl, substituted $C_{2-4}$-alkenyl, $C_{1-4}$-alkyl substituted with phenyl optionally substituted with 1–5 substituents or with pyridyl optionally substituted with 1–4 substituents selected from $C_{1-4}$-alkyl, $C_{1-4}$-alkoxy, hydroxy, fluorine, chlorine and bromine, wherein substituted $C_{2-4}$-alkenyl is substituted with 1–2 substituents selected from cyano, amino-carbonyl and $C_{1-4}$-alkyl-oxy-carbonyl, or A is a group of formula Z—$CH_2$—Y—$CH_2$—, wherein Y is O or NR wherein R is hydrogen or $C_{1-4}$-alkyl and Z is pyridyl or optionally substituted phenyl with 1–3 benzyl-oxy groups;

X is S or O;

with the provisos that
(i) only one of $R^1$ and $R^2$ is hydrogen;
(ii) when X is O, then $R^1$ cannot be aryl;

as well as hydrolyzable esters or ethers of compounds of formula I and pharmaceutically acceptable salts thereof.

Further preferred embodiments of the invention are compounds of formula I wherein $R^1$ is $C_{1-7}$-alkyl,
preferred wherein
$R^1$ is $C_{1-4}$-alkyl,
more preferred wherein
$R^1$ is isopropyl;
$R^2$ is $C_{1-7}$-alkyl,
preferred wherein
$R^2$ is $C_{1-4}$-alkyl,
more preferred wherein
$R^2$ is methyl or ethyl,
most preferred wherein
$R^2$ is methyl;
$R^3$ is optionally substituted phenyl,
wherein phenyl may be substituted with 1–5 substituents selected from $C_{1-4}$-alkyl, $C_{1-4}$-alkoxy, hydroxy, fluorine, chlorine, bromine and cyano,
preferred wherein
$R^3$ is optionally substituted phenyl,
wherein phenyl may be substituted with 1–3 substituents selected from $C_{1-2}$-alkyl, $C_{1-2}$-alkoxy, hydroxy, fluorine, chlorine, bromine and cyano,
more preferred wherein
$R^3$ is optionally substituted phenyl,
wherein phenyl may be substituted with 1–3 chlorine substituents;,
most preferred wherein
$R^3$ is optionally substituted phenyl,
wherein phenyl may be substituted with 1–2 chlorine substituents;
A is $C_{1-4}$-alkyl substituted with phenyl optionally substituted with 1–3 substituents or with pyridyl optionally substituted with 1–2 substituents selected from $C_{1-4}$-alkyl, $C_{1-4}$-alkoxy, hydroxy, fluorine, chlorine and bromine, or
A is a group of formula Z—$CH_2$—Y—$CH_2$—,
wherein Y is O or NR wherein R is hydrogen or $C_{1-4}$-alkyl and
Z is pyridyl or phenyl,
preferred wherein
A is $C_{1-2}$-alkyl substituted with phenyl optionally substituted with 1–3 substituents or with pyridyl optionally substituted with 1–2 substituents selected from $C_{1-4}$-alkyl, $C_{1-4}$-alkoxy, hydroxy, fluorine, chlorine and bromine, or
A is a group of formula Z—$CH_2$—Y—$CH_2$—,
wherein Y is O or NR wherein R is hydrogen or $C_{1-2}$-alkyl and
Z is pyridyl or phenyl,
more preferred wherein
A is $C_{1-2}$-alkyl substituted with phenyl or pyridyl, or
A is a group of formula Z—$CH_2$—Y—$CH_2$—,
wherein Y is O or NR wherein R is hydrogen or $C_{1-2}$-alkyl and
Z is pyridyl or phenyl, most preferred wherein A is $C_{1-2}$-alkyl substituted with pyridyl, or A is a group of formula Z—$CH_2$—Y—$CH_2$—, wherein Y is O or NR wherein R is hydrogen or $C_{1-2}$-alkyl and Z is pyridyl;

X is S or O;

as well as hydrolyzable esters or ethers of compounds of formula I and pharmaceutically acceptable salts thereof.

Another embodiment of the invention are compounds of formula I wherein $R^1$ is hydrogen, $C_{1-12}$-alkyl, $C_{3-8}$-cycloalkyl, aryl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine;

$R^2$ is hydrogen, $C_{1-12}$-alkyl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine;

$R^3$ is $C_{1-12}$-alkyl, $C_{3-8}$-cycloalkyl, phenyl or benzyl,
wherein a phenyl ring may be substituted with 1–5 substituents selected from $C_{1-4}$-alkyl, $C_{1-4}$-alkoxy, hydroxy, fluorine, chlorine and bromine;

A is hydroxy-$C_{1-4}$-alkyl or aryl-CH(OH)—; or

A is a group of formula Z—$CH_2$—Y—$CH_2$—, wherein Y is O or NR wherein R is hydrogen or $C_{1-4}$-alkyl and Z is aryl or heterocyclyl; or A is $C_{1-4}$-alkyl substituted with phenyl optionally substituted with 1–5 substituents or with heterocyclyl optionally substituted with 1–4 substituents selected from $C_{1-4}$-alkyl, $C_{1-4}$-alkoxy, hydroxy, fluorine, chlorine and bromine;

X is S or O;

with the proviso that only one of $R^1$ and $R^2$ is hydrogen;

as well as hydrolyzable esters or ethers of compounds of formula I and pharmaceutically acceptable salts thereof.

An especially preferred embodiment of the invention are compounds of formula I wherein X is S;

as well as hydrolyzable esters or ethers of compounds of formula I and pharmaceutically acceptable salts thereof.

More preferred embodiments of compounds of formula I, as well as hydrolyzable esters or ethers of compounds of formula I and pharmaceutically acceptable salts thereof, are listed in table 1:

TABLE 1

| STRUCTURE | SYSTEMATIC NAME |
|---|---|
| 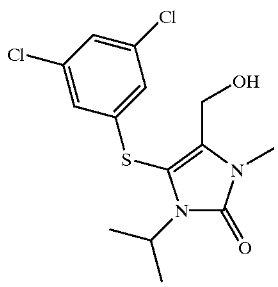 | 4-(3,5-Dichlorophenylthio)-5-hydroxymethyl-3-isopropyl-1-methyl-1,3-dihydro-2-imidazolone |
| 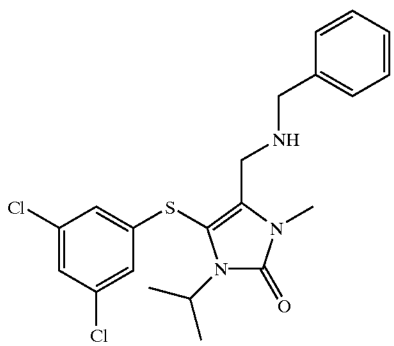 | 5-(Benzylaminomethyl)-4-(3,5-dichlorophenylthio)-3-isopropyl-1-methyl-1,3-dihydro-2-imidazolone |
| 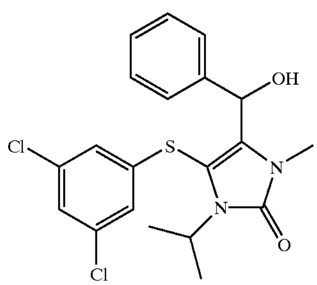 | 4-(3,5-Dichlorophenylthio)-5-(alpha(RS)-hydroxybenzyl)-3-isopropyl-1-methyl-1,3-dihydro-2-imidazolone |
| 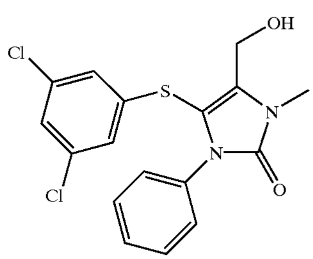 | 4-(3,5-Dichlorophenylthio)-5-hydroxymethyl-1-methyl-3-phenyl-1,3-dihydro-2-imidazolone |
| 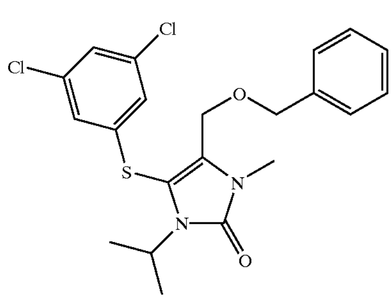 | 5-Benzyloxymethyl-4-(3,5-dichlorophenylthio)-3-isopropyl-1-methyl-1,3-dihydro-2-imidazolone |

TABLE 1-continued

| STRUCTURE | SYSTEMATIC NAME |
| --- | --- |
| 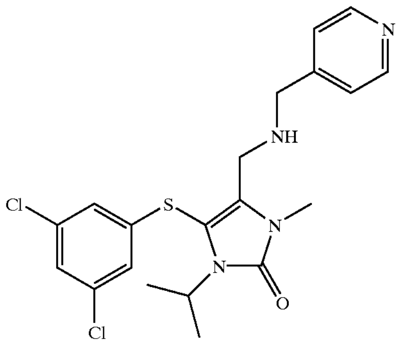 | 4-(3,5-Dichlorophenylthio)-3-isopropyl-1-methyl-5-{[(pyridin-4-ylmethyl)-amino]-methyl}-1,3-dihydro-2-imidazolone |
| 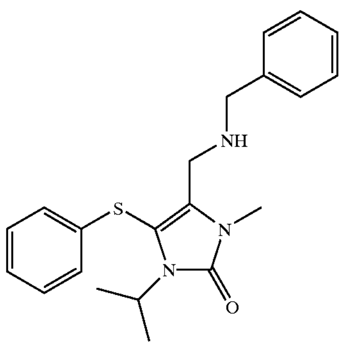 | 5-(Benzylaminomethyl)-3-isopropyl-1-methyl-4-phenylthio-1,3-dihydro-2-imidazolone |
| 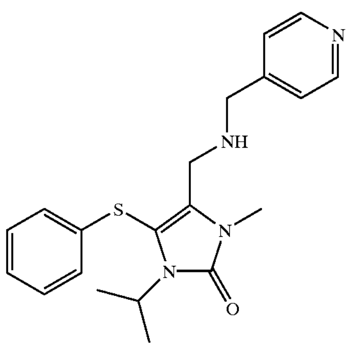 | 3-Isopropyl-1-methyl-4-phenylthio-5-{[(pyridin-4-ylmethyl)amino]methyl}-1,3-dihydro-2-imidazolone |
| 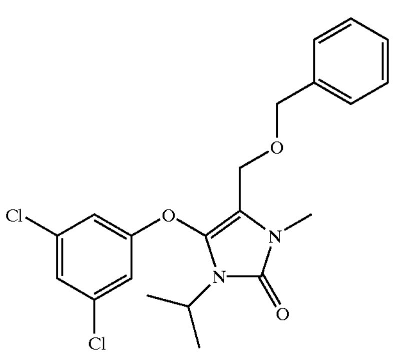 | 5-Benzyloxymethyl-4-(3,5-dichlorophenoxy)-3-isopropyl-1-methyl-1,3-dihydro-2-imidazolone |

TABLE 1-continued

| STRUCTURE | SYSTEMATIC NAME |
|---|---|
| 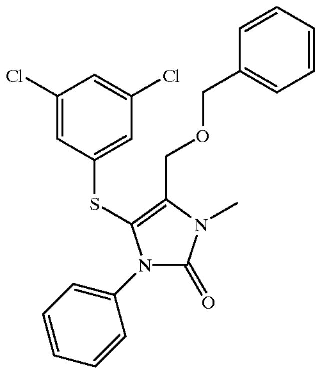 | 5-Benzyloxymethyl-4-(3,5-dichlorophenylthio)-1-methyl-3-phenyl-1,3-dihydro-2-imidazolone |
| 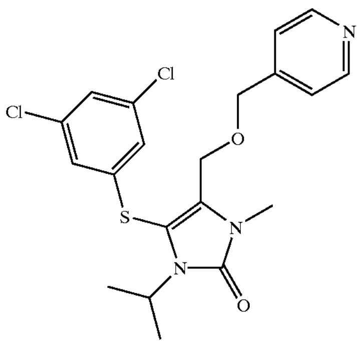 | 4-(3,5-Dichlorothio)-3-isopropyl-1-methyl-5-(pyridin-4-ylmethoxymethyl)-1,3-dihydro-2-imidazolone |
| 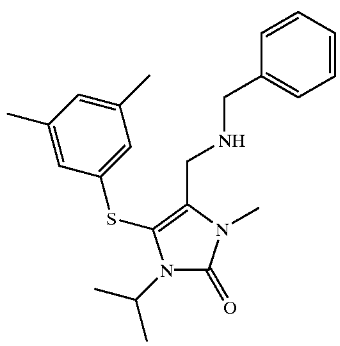 | 5-(Benzylaminomethyl)-4-(3,5-dimethylphenylthio)-3-isopropyl-1-methyl-1,3-dihydro-2-imidazolone |
| 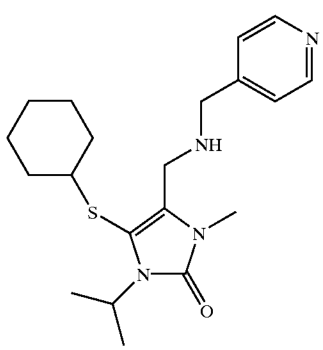 | 4-Cyclohexylthio-3-isopropyl-1-methyl-5-{[(pyridin-4-ylmethyl)amino]-methyl}-1,3-dihydro-2-imidazolone |

TABLE 1-continued

| STRUCTURE | SYSTEMATIC NAME |
| --- | --- |
| 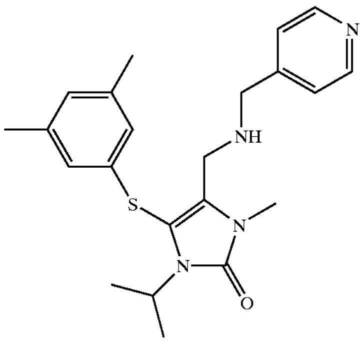 | 4-(3,5-Dimethylphenythio)-3-isopropyl-1-methyl-5-{[(pyridin-4-ylmethyl)-amino]methyl}-1,3-dihydro-2-imidazolone |
| 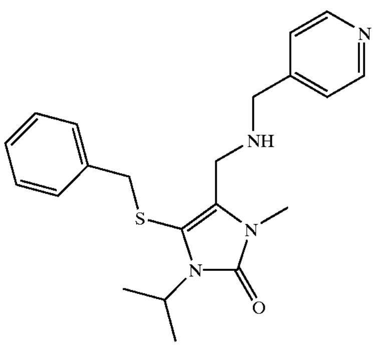 | 4-Benzylthio-3-isopropyl-1-methyl-5-{[(pyridin-4-ylmethyl)amino]methyl}-1,3-dihydro-2-imidazolone |
| 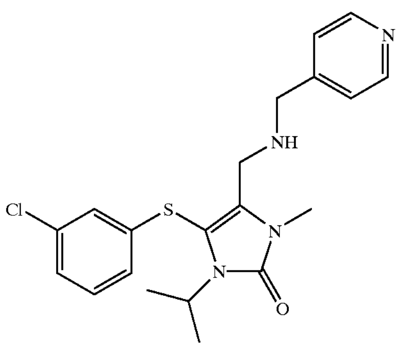 | 4-(3-Chlorophenylthio)-3-isopropyl-1-methyl-5-{[(pyridin-4-ylmethyl)-amino]methyl}-1,3-dihydro-2-imidazolone |
| 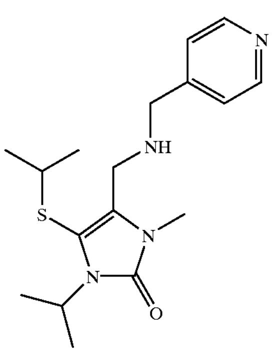 | 3-Isopropyl-4-isopropylthio-1-methyl-5-{[(pyridin-4-ylmethyl)amino]-methyl}-1,3-dihydro-2-imidazolone |

TABLE 1-continued

| STRUCTURE | SYSTEMATIC NAME |
|---|---|
| 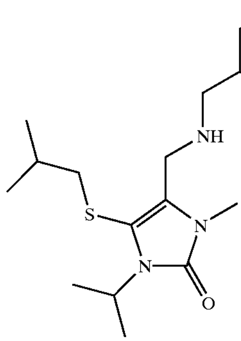 | 4-Isobutylthio-3-isopropyl-1-methyl-5-{[(pyridin-4-ylmethyl)amino]methyl}-1,3-dihydro-2-imidazolone |
| 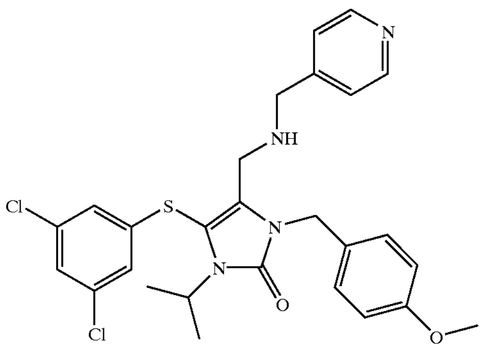 | 4-(3,5-Dichlorophenylthio)-3-isopropyl-1-(4-methoxybenzyl)-5-{[(pyridin-4-ylmethyl)amino]methyl}-1,3-dihydro-2-imidazolone |
| 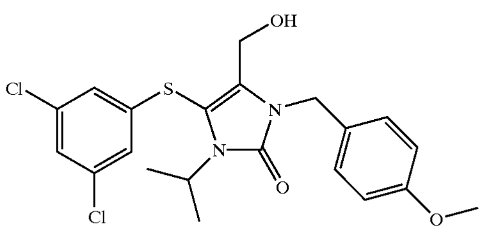 | 4-(3,5-Dichlorophenylthio)-5-hydroxymethyl-3-isopropyl-1-(4-methoxybenzyl)-1,3-dihydro-2-imidazolone |
| 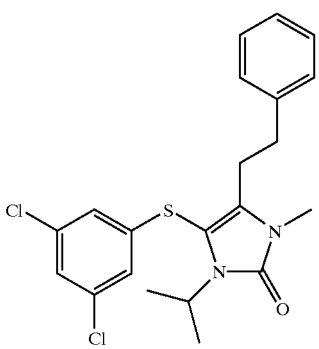 | 4-(3,5-Dichlorophenylthio)-3-isopropyl-1-methyl-5-phenethyl-1,3-dihydro-2-imidazolone |
| 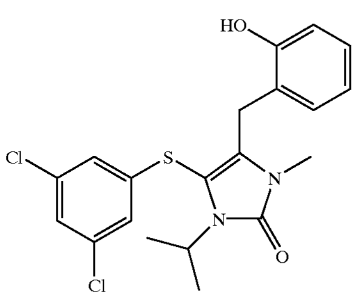 | 4-(3,5-Dichlorophenylthio)-5-(2-hydroxybenzyl)-3-isopropyl-1-methyl-1,3-dihydro-2-imidazolone |

TABLE 1-continued

| STRUCTURE | SYSTEMATIC NAME |
|---|---|
| 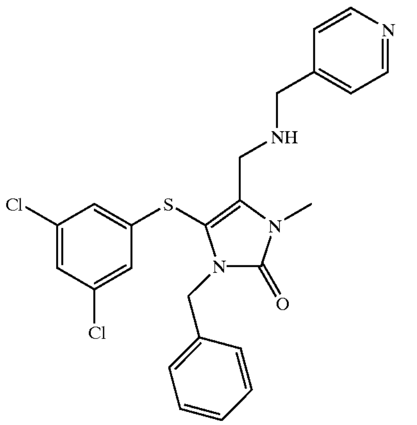 | 3-Benzyl-4-(3,5-dichlorophenylthio)-1-methyl-5-{[(pyridin-4-ylmethyl)-amino]methyl}-1,3-dihydro-2-imidazolone |
| 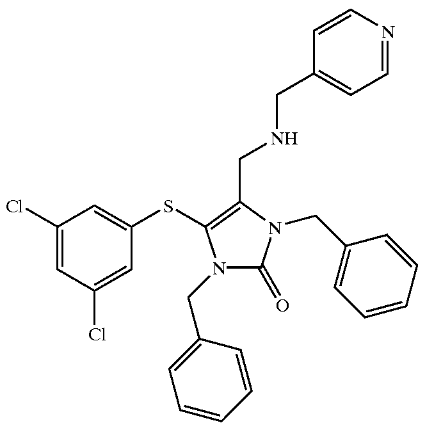 | 1,3-Dibenzyl-4-(3,5-dichlorophenylthio)-5-{[(pyridin-4-ylmethyl)amino]-methyl}-1,3-dihydro-2-imidazolone |
| 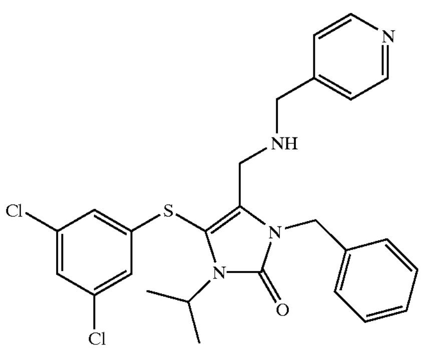 | 1-Benzyl-4-(3,5-dichlorophenylthio)-3-isopropyl-5-{[(pyridin-4-ylmethyl)-amino]methyl}-1,3-dihydro-2-imidazolone |
| 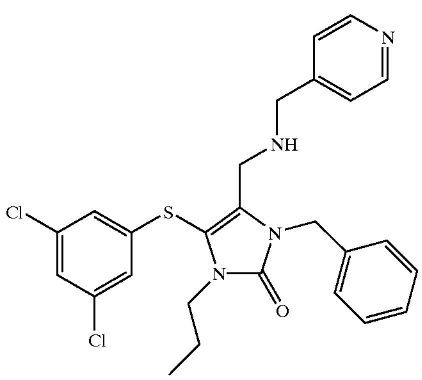 | 1-Benzyl-4-(3,5-dichlorophenylthio)-3-propyl-5-{[(pyridin-4-ylmethyl)-amino]methyl}-1,3-dihydro-2-imidazolone |

TABLE 1-continued

| STRUCTURE | SYSTEMATIC NAME |
|---|---|
| 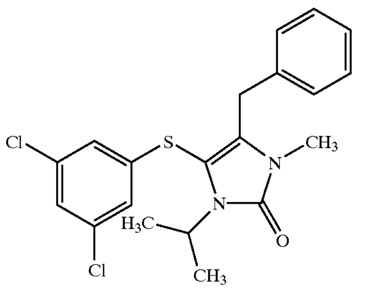 | 5-Benzyl-4-(3,5-dichlorophenylthio)-3-isopropyl-1-methyl-1,3-dihydro-2-imidazolone |
| 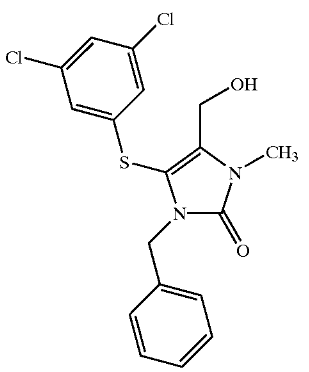 | 3-Benzyl-4-(3,5-dichlorophenylthio)-5-hydroxymethyl-1-methyl-1,3-dihydro-2-imidazolone |
| 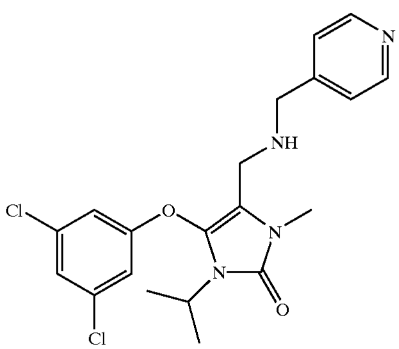 | 4-(3,5-Dichlorophenoxy)-3-isopropyl-1-methyl-5-{[(pyridin-4-ylmethyl)-amino]methyl}-1,3-dihydro-2-imidazolone |
| 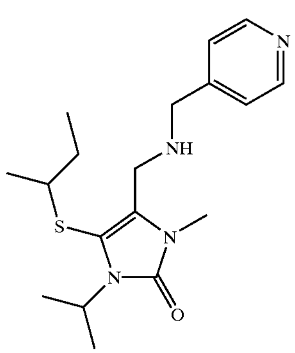 | 4-sec-Butylthio-3-isopropyl-1-methyl-5-{[(pyridin-4-ylmethyl)amino]-methyl}-1,3-dihydro-2-imidazolone |

TABLE 1-continued

| STRUCTURE | SYSTEMATIC NAME |
|---|---|
| 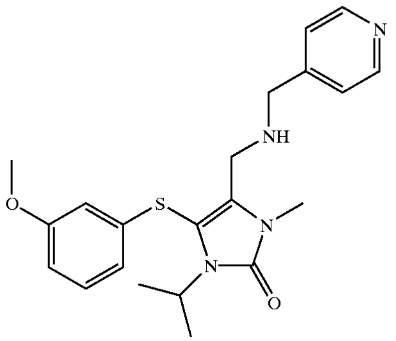 | 3-Isopropyl-4-(3-methoxyphenylthio)-1-methyl-5-{[(pyridin-4-ylmethyl)-amino]methyl}-1,3-dihydro-2-imidazolone |
| 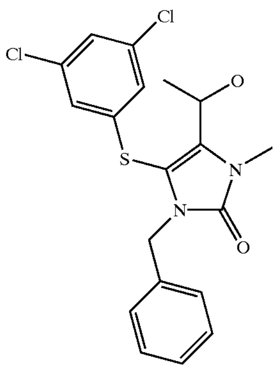 | 3-Benzyl-4-(3,5-dichlorophenylthio)-5-(1-hydroxyethyl)-1-methyl-1,3-dihydro-2-imidazolone |
| 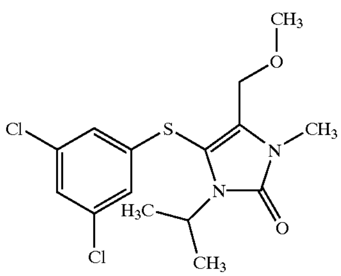 | 4-(3,5-Dichloro-phenylsulfanyl)-3-isopropyl-5-methoxymethyl-1-methyl-1,3-dihydro-imidazol-2-one |
| 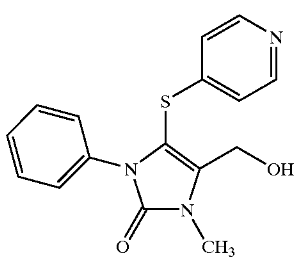 | 4-Hydroxymethyl-3-methyl-1-phenyl-5-(pyridin-4-ylsulfanyl)-1,3-dihydro-imidazol-2-one |
| ClH | 1-Benzyl-4-hydroxymethyl-3-methyl-5-(pyridin-4-ylsulfanyl)-1,3-dihydro-imidazol-2-one; hydrochloric acid |

TABLE 1-continued

| STRUCTURE | SYSTEMATIC NAME |
| --- | --- |
| 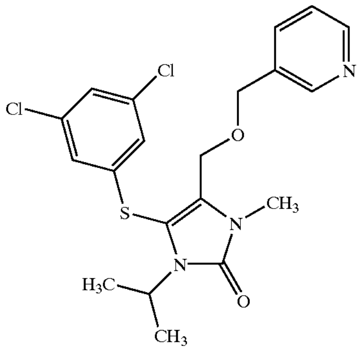 | 4-(3,5-Dichloro-phenylsulfanyl)-3-isopropyl-1-methyl-5-(pyridin-3-yl-methoxymethyl)-1,3-dihydro-imidazol-2-one |
| 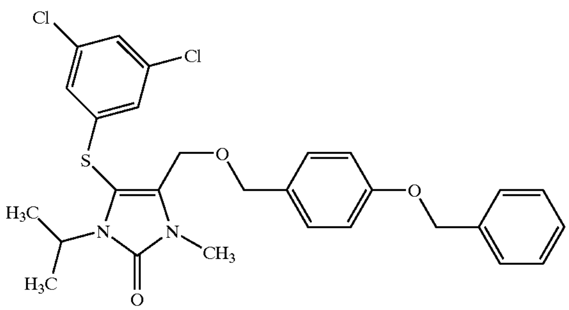 | 4-(4-Benzyloxy-benzyloxymethyl)-5-(3,5-dichloro-phenylsulfanyl)-1-isopropyl-3-methyl-1,3-dihydro-imidazol-2-one |
| 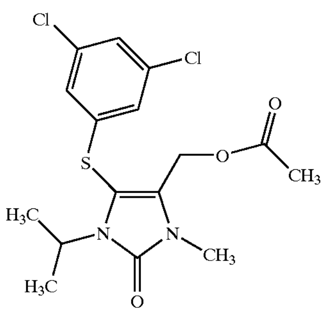 | Acetic acid 5-(3,5-dichloro-phenylsulfanyl)-1-isopropyl-3-methyl-2-oxo-2,3-dihydro-1H-imidazol-4-ylmethyl ester |
| 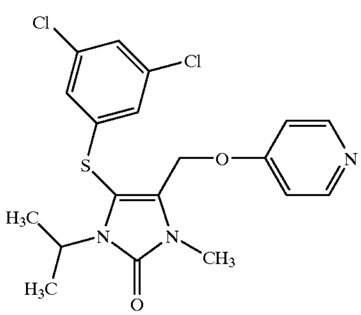 | 3-(3,5-Dichloro-phenylsulfanyl)-3-isopropyl-1-methyl-5-(pyridin-4-yloxy-methyl)-1,3-dihydro-imidazol-2-one |
| 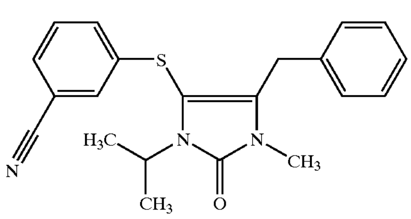 | 3-(5-Benzyl-3-isopropyl-1-methyl-2-oxo-2,3-dihydro-1H-imidazol-4-ylsulfanyl)-benzonitrile |

TABLE 1-continued

| STRUCTURE | SYSTEMATIC NAME |
|---|---|
| 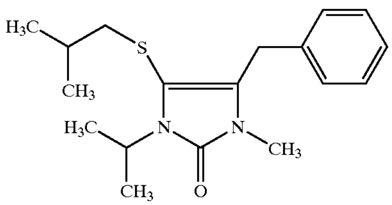 | 4-Benzyl-5-isobutylsulfanyl-1-isopropyl-3-methyl-1,3-dihydro-imidazol-2-one |
| 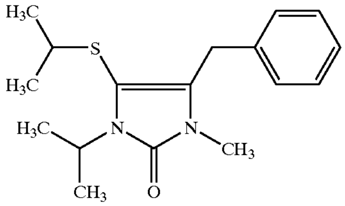 | 4-Benzyl-1-isopropyl-5-isopropylsulfanyl-3-methyl-1,3-dihydro-imidazol-2-one |
| 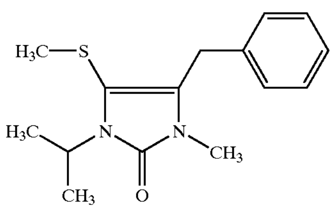 | 4-Benzyl-1-isopropyl-3-methyl-5-methylsulfanyl-1,3-dihydro-imidazol-2-one |
| 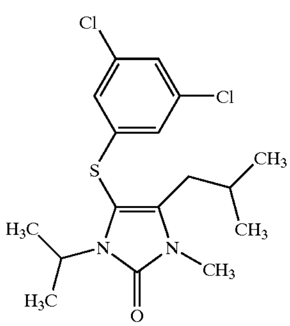 | 4-(3,5-Dichloro-phenylsulfanyl)-5-isobutyl-3-isopropyl-1-methyl-1,3-dihydro-imidazol-2-one |
| 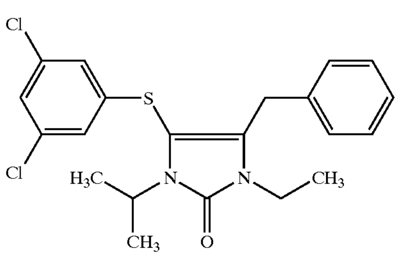 | 4-Benzyl-5-(3,5-dichloro-phenylsulfanyl)-3-ethyl-1-isopropyl-1,3-dihydro-imidazol-2-one |
| 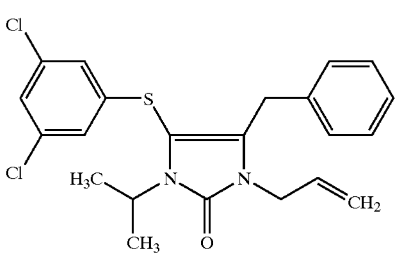 | 1-Allyl-5-benzyl-4-(3,5-dichloro-phenylsulfanyl)-3-isopropyl-1,3-dihydro-imidazol-2-one |

TABLE 1-continued

| STRUCTURE | SYSTEMATIC NAME |
|---|---|
| 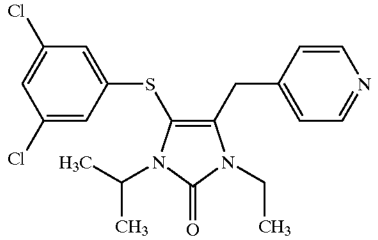 | 4-(3,5-Dichloro-phenylsulfanyl)-1-ethyl-3-isopropyl-5-pyridin-4-ylmethyl-1,3-dihydro-imidazol-2-one |
| 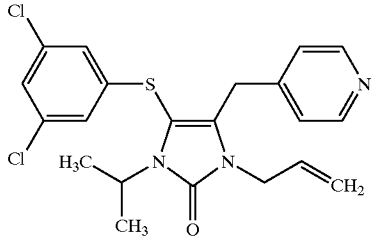 | 1-Allyl-4-(3,5-dichloro-phenylsulfanyl)-3-isopropyl-5-pyridin-4-ylmethyl-1,3-dihydro-imidazol-2-one |
| 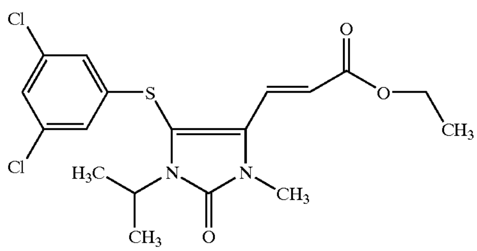 | [E]-3-[5-(3,5-Dichloro-phenylsulfanyl)-1-isopropyl-3-methyl-2-oxo-2,3-dihydro-1H-imidazol-4-yl]-acrylic acid ethyl ester |
| 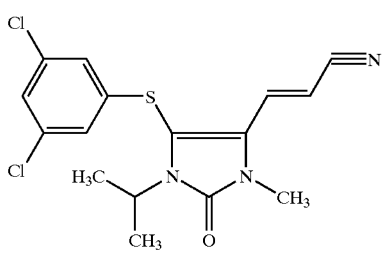 | 3-[5-(3,5-Dichloro-phenylsulfanyl)-1-isopropyl-3-methyl-2-oxo-2,3-dihydro-1H-imidazol-4-yl]-acrylonitrile |
| 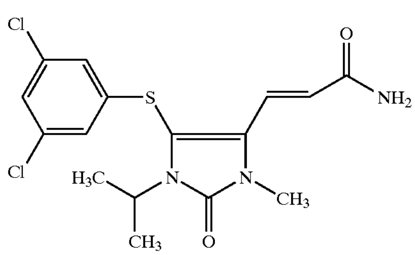 | 3-[5-(3,5-Dichloro-phenylsulfanyl)-1-isopropyl-3-methyl-2-oxo-2,3-dihydro-1H-imidazol-4-yl]-acrylamide |
| 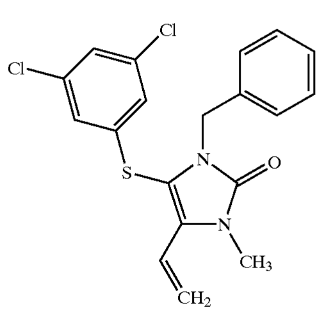 | 1-Benzyl-5-(3,5-dichloro-phenylsulfanyl)-3-methyl-4-vinyl-1,3-dihydro-imidazol-2-one |

| STRUCTURE | SYSTEMATIC NAME |
|---|---|
| 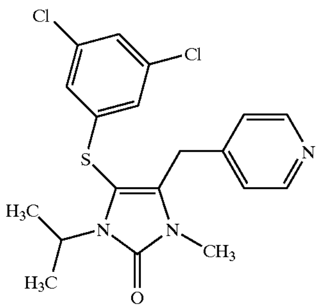 | 3-(3,5-Dichloro-phenylsulfanyl)-3-isopropyl-1-methyl-5-pyridin-5-ylmethyl-1,3-dihydro-imidazol-2-one |

The imidazolone derivatives provided by the present invention are useful in the treatment of the human or animal body.

The imidazolone derivatives provided by the present invention are inhibitors of the human immunodeficiency virus reverse transcriptase enzyme. Accordingly, the present imidazolone derivatives are therapeutically active substances in the treatment of diseases mediated by the human immunodeficiency virus (HIV) and can be used as medicaments for the treatment of such diseases.

They can be used as medicaments, especially for treating viral diseases, immune mediated conditions or diseases, bacterial diseases, parasitic diseases, inflammatory diseases, hyperproliferative vascular diseases, tumors, and cancer.

In particular, compounds of the present invention and pharmaceutical compositions containing the same are useful as chemotherapeutic agents, inhibitors of viral replication and modulators of the immune system, and can be used for the treatment of diseases mediated by the human immunodeficiency virus (HIV) other viral diseases such as retroviral infections (either alone or in combination with other antiviral agents such as interferon or derivatives thereof, such as conjugates with polyethylene glycol).

They can be used alone, or in combination with other therapeutically active agents, for example, an immunosuppressant, a chemotherapeutic agent, an anti-viral agent, an antibiotic, an anti-parasitic agent, an anti-inflammatory agent, an anti-fungal agent and/or an anti-vascular hyperproliferation agent.

Compounds, whenever prepared by the processes of the present invention are also an object of the present invention.

The compounds of the present invention can be prepared as shown in the following scheme:

Reaction scheme 1:

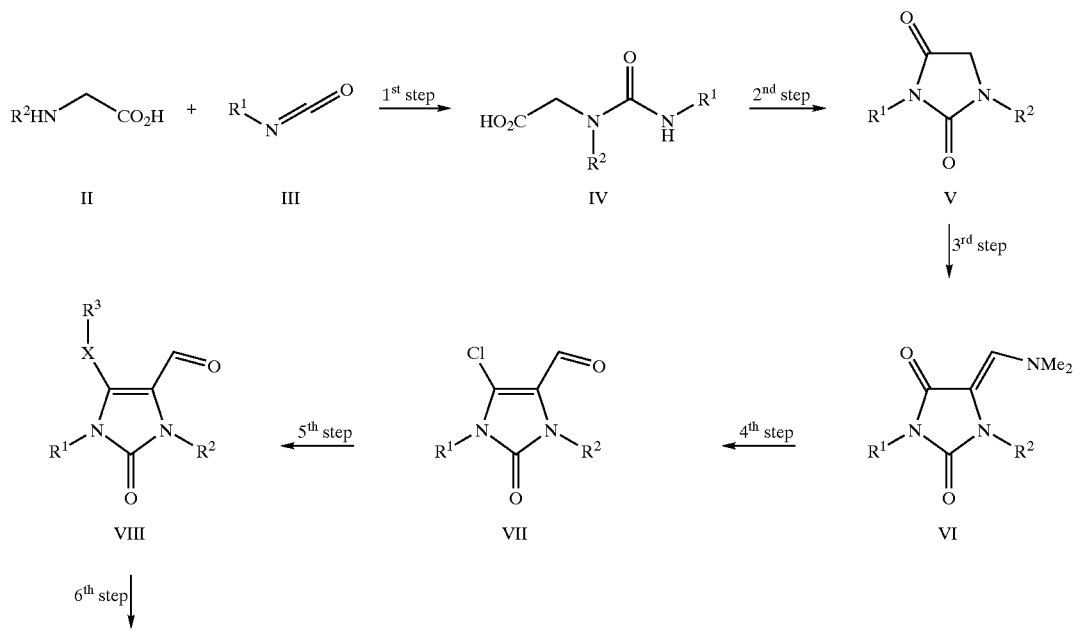

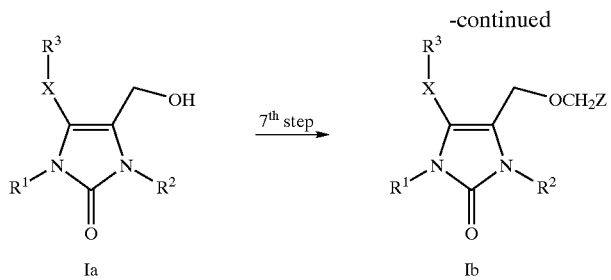

wherein $R^1$, $R^2$, $R^3$, X and Z are as defined for compounds of formula I.

In accordance with the present invention, the preparation of compounds of formula

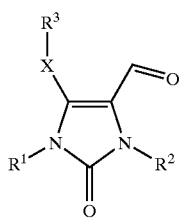

VIII wherein $R^1$, $R^2$, $R^3$ and X are as defined in formula I; comprises reacting chloro compound of formula VII

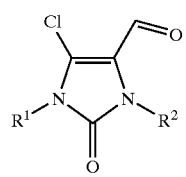

VII wherein $R^1$ and $R^2$ are as defined in formula I
with nucleophilic agent $R^3XH$
wherein $R^3$ and X are as defined in formula I.

The reaction is described in more detail in reaction scheme 1 (fifth reaction step).

In reaction scheme 1, the first reaction step is carried out in that glycine derivative of formula II (commercially available or prepared according to known methods in the art for example alkylation reaction of the nitrogen function of glycine) is reacted with an isocyanate derivative of formula III (commercially available or synthesised according to known methods from textbooks on organic chemistry e.g. from J. March (1992), "Advanced Organic Chemistry: Reactions, Mechanisms and Structure", 4$^{th}$ ed. John Wiley and Sons) in an appropriate solvent, in the presence of 0.5–1.5 equivalents, preferably 0.7–1.3 equivalents, most preferred 0.9 equivalents of a base such as potassium carbonate, sodium carbonate, magnesium carbonate, calcium carbonate, potassium hydroxide, sodium hydroxide, magnesium hydroxide, calcium hydroxide, $N(CH_3)_3$, $N(C_2H_5)_3$, $N(n-C_3H_7)_3$, $N(iso-C_3H_7)_3$, preferably sodium hydroxide. The reaction is conveniently carried out at a reaction temperature from −5° C. to boiling temperature of the reaction mixture, preferably at a reaction temperature between 0° C. and about 80° C. The reaction can optionally be carried out under an inert atmosphere such as nitrogen or argon atmosphere. An appropriate solvent may be water or an organic solvent such as alcohols (e.g. methanol, ethanol, propanol, butanol, octanol or cyclohexanol), ethers (e.g. tetrahydrofuran, diethyl ether, dibutyl ether or dioxane), halogenated hydrocarbons (e.g. dichloromethane or trichloromethane), hydrocarbons (e.g. cyclohexane, methyl cyclohexane, decaline, benzene, toluene, o-xylene, m-xylene or p-xylene) or a mixtures of the mentioned solvents, preferably water. After the reaction, the system is neutralised with an acid, preferably a protic acid such as HBr, HI, AcOH or citric acid, most preferred HCl, to yield the urea of formula IV.

In the second step of the reaction, urea of formula IV is converted in a ring-closure reaction to imidazoldione derivatives of formula V by dissolving compound of formula IV in water and an acid, preferably a protic acid such as HCl, HBr, HI, AcOH, citric or other, most preferred HCl. The reaction is conveniently carried out at a reaction temperature from room temperature to boiling temperature of the reaction mixture, preferably at a reaction temperature from 60° C. to boiling temperature of the reaction mixture. The reaction can optionally be carried out in an inert organic solvent such as ethers (e.g. tetrahydrofuran, diethyl ether, dibutyl ether or dioxane), polar aprotic solvents such as dimethylsulfoxide (DMSO) or dimethylacetamide, halogenated hydrocarbons such as dichloromethane or trichloromethane, hydrocarbons such as cyclohexane, methyl cyclohexane, decaline, benzene, toluene, o-xylene, m-xylene or p-xylene, or mixtures of the mentioned solvents.

In the third step of the reaction, imidazoldione derivatives of formula V is reacted with di-$C_{1-4}$-alkylacetal of dimethylformamide, preferably dimethylformamide dimethylacetal (commercially available or synthesized according to methods known from textbooks about organic chemistry e.g. from J. March (1992), "Advanced Organic Chemistry: Reactions, Mechanisms, and Structure", 4$^{th}$ ed. John Wiley & Sons) to attach a dimethylaminomethylene group to the imidazoldione ring and to obtain the corresponding compound of formula VI. The reaction is carried out at a reaction temperature from room temperature to boiling temperature of the reaction mixture, preferably at a reaction temperature from 60° C. to boiling temperature of the reaction mixture, most preferred at a reaction temperature from 80° C. to boiling temperature of the reaction mixture. The reaction can optionally be carried out in an inert organic solvent such as ethers (e.g. tetrahydrofuran, diethyl ether, dibutyl ether or dioxane), polar aprotic solvents such as dimethylsulfoxide (DMSO), halogenated hydrocarbons such as dichloromethane or trichloromethane, hydrocarbons such as cyclohexane, methyl cyclohexane, decaline, benzene, toluene, o-xylene, m-xylene or p-xylene, or mixtures of the mentioned solvents.

In the fourth step of the reaction, dimethylaminomethylene imidazoldione derivatives of formula VI are converted to the corresponding carbaldehyde chloro imidazolone compound of formula VII as described in U.S. Pat. No. 4,345,936 or known from textbooks about organic chemistry. The reaction which includes a dimethylaminomethylene/carbaldehyde and oxo/chlorine exchange may be carried out in the presence of a disubstituted formamide such as N,N-dimethylformamide, N,N-methylphenylformamide or N,N-diphenylformamide, preferably dimethylformamide in the presence of $POCl_3$ according the Vilsmeier reaction or in the presence of other chlorinating agents such as $PCl_5$, $SOCl_2$ or $(COCl)_2$. The reaction is optionally carried out under an inert atmosphere such as nitrogen or argon atmosphere at a reaction temperature from room temperature to boiling temperature of the reaction mixture, preferably at a reaction temperature between about 50° C. and about 150° C. The reaction can optionally be carried out in an inert organic solvent such as ethers (e.g. tetrahydrofuran, diethyl ether, dibutyl ether or dioxane), polar aprotic solvents such as dimethylsulfoxide (DMSO) or N,N-dimethylacetamide, halogenated hydrocarbons such as dichloromethane or trichloromethane, hydrocarbons such as cyclohexane, methyl cyclohexane, decaline, benzene, toluene, o-xylene, m-xylene or p-xylene, or a mixtures of the mentioned solvents.

In the fifth step of the reaction, chloro compounds of formula VII are reacted with nucleophilic thiol $R^3SH$ or nucleophilic alcohol $R^3OH$ (both agents are commercially available or can be synthesized according to methods known from textbooks about organic chemistry e.g. from J. March (1992), "Advanced Organic Chemistry: Reactions, Mechanisms, and Structure", $4^{th}$ ed. John Wiley & Sons, to obtain the corresponding compound of formula VIII. The reaction is carried out in an appropriate solvent in the presence of a suitable base such as n-BuLi, sodium hydride, trialkylamine (e.g. trimethylamine or triethylamine), potassium carbonate, sodium carbonate, magnesium carbonate, calcium carbonate, preferably triethylamine, N-methyl morpholine or potassium carbonate. The reaction is conveniently carried out under an inert atmosphere such as nitrogen or argon atmosphere at a reaction temperature from 0° C. to boiling temperature of the reaction mixture, preferably at a reaction temperature between about 10° C. and about 60° C. Appropriate solvents for the reaction are ethers (e.g. tetrahydrofuran, diethyl ether, dibutyl ether or dioxane), polar aprotic solvents such as dimethylsulfoxide (DMSO) or N,N-dimethylacetamide, halogenated hydrocarbons such as dichloromethane or trichloromethane, hydrocarbons such as cyclohexane, methyl cyclohexane, decaline, benzene, toluene, o-xylene, m-xylene or p-xylene, or a mixtures of the mentioned solvents, preferably dichloromethane or trichloromethane.

Also part of the present invention are novel compounds of formula VIII-a

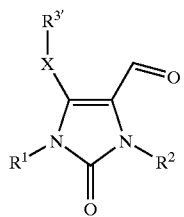

VIII-a wherein $R^1$, $R^2$ and X are as defined in formula I and $R^{3'}$is $C_{7-12}$-alkyl, $C_{3-8}$-cycloalkyl, optionally substituted phenyl or optionally substituted benzyl wherein phenyl or benzyl may be substituted with 1–5 substituents selected from $C_{1-4}$-alkyl, $C_{1-4}$-alkoxy, hydroxy, fluorine, chlorine or bromine In the sixth step of the reaction, the aldehyde of formula VIII is reduced in the presence of a reducing agent to obtain the corresponding alcohol derivative of formula Ia. Reducing agents conveniently used for the reaction are preferably sodium borohydride or other reducing agents such as lithium borohydride, sodium triacetoxyborohydride, hydrogen over a catalyst or reducing agents known in the art applied according to known methods described in textbooks on organic chemistry e.g. from J. March (1992), "Advanced Organic Chemistry: Reactions, Mechanisms and Structure", $4^{th}$ ed. John Wiley and Sons. The reduction reaction is conveniently carried out in an organic solvent for example alcoholic solvents such as methanol, ethanol, propanol, butanol, octanol or cyclohexanol, preferably methanol or ethanol or ethers such as tetrahydrofuran, diethyl ether, dibutyl ether, dioxane or diglyme, preferably tetrahydrofuran or a mixture of the mentioned solvents such as methanol and tetrahydrofuran or ethanol and tetrahydrofuran. The reaction is carried out at a reaction temperature between about −10° C. and about 60° C., preferably at room temperature. The reduction reaction can also be carried out as described in textbooks about organic chemistry e.g. from J. March (1992), "Advanced Organic Chemistry: Reactions, Mechanisms, and Structure", $4^{th}$ ed. John Wiley & Sons.

In the seventh step of the reaction, the alcohol derivative of formula Ia is derivatized to the corresponding ether derivative of formula Ib. The derivatisation reaction is conveniently carried out with an electophilic agent L—$CH_2$—Z, wherein Z is as defined for compounds of formula I and L is a leaving group such as bromide, chloride, iodide, tosylate, triflate or any other according to methods known from textbooks on organic chemistry e.g. from J. March (1992), "Advanced Organic Chemistry: Reactions, Mechanisms and Structure", $4^{th}$ ed. John Wiley and Sons). The reaction is carried out as described in the literature, for example in the presence of a base such as sodium hydride, lithium hydride, potassium carbonate or triethylamine in an appropriate organic solvent such as tetrahydrofuran (THF) or polar aprotic solvents like dimethylsulfoxide (DMSO), N,N-dimethylacetamide or N,N-dimethylformamide (DMF), preferably DMF or THF, at a reaction temperature between about −10° C. and about 60° C., preferably at room temperature.

For the synthesis of compounds of formula Ia or Ib wherein $R^1$, $R^3$, X and Z are as defined for compounds of formula I and $R^2$ is hydrogen, the corresponding compound of formula VI is N-protected with an appropriate protecting group for example 4-methoxybenzyl, benzyl or 3,4-dimethoxybenzyl and then further reacted according the reaction steps 4–6 (and optionally 7), and finally deprotected according to methods known from textbooks on protecting chemistry ('Protecting Groups in Organic Synthesis', second edition, Theodora W. Greene and Peter G. M. Wuts, Wiley-Interscience, 1991) for example in the presence of hydrogen and appropriate catalyst such as Pd/C or Pt/C. Compounds of formula Ia or Ib wherein $R^1$, $R^3$, X and Z are as defined for compounds of formula I and $R^2$ is hydrogen are obtained. The protecting reaction is for example carried out in a polar aprotic solvents like dimethylsulfoxide (DMSO), dimethylacetamide or N,N-dimethylformamide (DMF), preferably dimethylformamide in the presence of a base such as lithium hydride or sodium hydride, preferably sodium hydride at a reaction temperature between about −10° C. and about 60° C., preferably at room temperature. The reaction system is then treated with an appropriate protecting agent such as 4-methoxybenzyl chloride, 4-methoxybenzyl bromide, benzyl chloride, benzyl bromide, 3,4-dimethoxybenzyl chloride or 3,4-dimethoxybenzyl bromide at a reaction temperature between about −10° C. and about 60° C., preferably at room temperature to obtain N-protected compound of formula VI. The deprotection reaction is carried out as described above.

For the synthesis of compounds of formula Ia or Ib wherein $R^2$, $R^3$, X and Z are as defined for compounds of formula I and $R^1$ is hydrogen, compound of formula III wherein $R^1$ is a N-protecting group known from the literature such as 4-methoxybenzyl, benzyl or 3,4-dimethoxybenzyl (commercially available or synthesized according to methods known from the literature) is reacted according reaction steps 1–6 (and optionally 7) and finally deprotected under conditions known from the literature. The protecting reaction is for example carried out in polar aprotic solvents like dimethylsulfoxide (DMSO), dimethylacetamide or N,N-dimethylformamide (DMF), preferably dimethylformamide in the presence of a base such as lithium hydride or sodium hydride, preferably sodium hydride at a reaction temperature between about −10° C. and about 60° C., preferably at room temperature. The reaction system is then treated with an appropriate protecting agent such as 4-methoxybenzyl chloride, 4-methoxybenzyl bromide, benzyl chloride, benzyl bromide, 3,4-dimethoxybenzyl chloride or 3,4-dimethoxybenzyl bromide at a reaction temperature between about −10° C. and about 60° C., preferably at room temperature to obtain N-protected compound of formula VI.

The deprotecting reaction is carried out for example under hydrogen in the presence of a catalyst such as palladium on charcoal or platinum on charcoal (as described above). The corresponding compound of formula Ia or Ib wherein $R^2$, $R^3$, X and Z are as defined for compounds of formula I and $R^1$ is hydrogen is obtained.

Optionally, compounds of formula Ia or Ib wherein $R^3$, X and Z are as defined for compounds of formula I, $R^1$ or $R^2$ is hydrogen and the other one of $R^1$ or $R^2$ is as defined for compounds of formula I, can also be converted to the corresponding compound of formula Ia or Ib wherein $R^1$, $R^2$, $R^3$, X and Z are as defined for compounds of formula I. The reaction is conveniently carried out with an electophilic agent $R^1$-L or $R^2$-L, wherein $R^1$ and $R^2$ is as defined for formula I but not hydrogen and L is a leaving group such as bromide, chloride, iodide, tosylate, triflate or any other according to methods known from textbooks on organic chemistry e.g. from J. March (1992), "Advanced Organic Chemistry: Reactions, Mechanisms and Structure", 4$^{th}$ ed. John Wiley and Sons). The reaction is carried out as described in the literature, for example in the presence of a base such as sodium hydride, lithium hydride, potassium carbonate or triethylamine in an appropriate organic solvent such as tetrahydrofuran (THF) or polar aprotic solvents like dimethylsulfoxide (DMSO), N,N-dimethylacetamide or N,N-dimethylformamide (DMF), preferably DMF or THF at a reaction temperature between about −10° C. and about 60° C., preferably at room temperature.

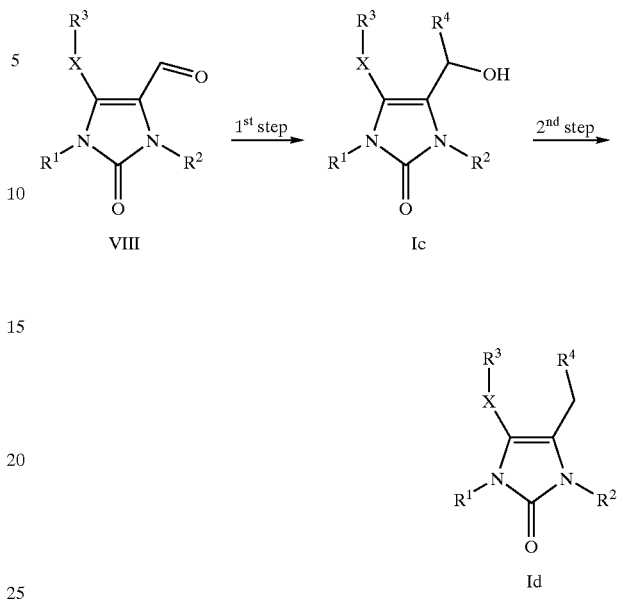

wherein $R^1$, $R^2$, $R^3$ and X are as defined for compounds of formula I and $R^4$ is alkyl, aryl, optionally substituted phenyl or optionally substituted heterocyclyl as defined for compounds of formula I or $C_{0-3}$-alkyl substituted with $C_{1-4}$-alkoxy, $C_{1-4}$-alkyl-carbonyl-oxy- or heterocyclyl-oxy or $R^4$ together with the methyl group forms a optionally substituted $C_{2-4}$-alkenyl as defined for compounds of formula I.

In reaction scheme 2, the first reaction step is carried out in that the aldehydes of formula VIII are derivatised with a Grignard reagent of formula $R^4$MgHal wherein $R^4$ is alkyl, aryl, optionally substituted phenyl or optionally substituted heterocyclyl as defined for compounds of formula I or $C_{0-3}$-alkyl substituted with $C_{1-4}$-alkoxy, $C_{1-4}$-alkyl-carbonyl-oxy- or heterocyclyl-oxy or $R^4$ together with the methyl group forms a optionally substituted $C_{2-4}$-alkenyl as defined for compounds of formula I, and Hal represents chlorine, bromine or iodine, preferably chlorine (commercially available or synthesised according to textbooks on organic chemistry e.g. from J. March (1992), "Advanced Organic Chemistry: Reactions, Mechanisms and Structure", 4$^{th}$ ed. John Wiley and Sons) to obtain the corresponding alcohol derivative of formula Ic. The derivatisation reaction is conveniently carried out in an inert solvent for example ethers such as tetrahydrofuran, diethyl ether, dibutyl ether, dioxane, diglyme or a mixture of the mentioned solvents, preferably tetrahydrofuran at a reaction temperature between about −10° C. and about 60° C., preferably at room temperature. In general, the derivatisation reaction can also be carried out as described in textbooks about organic chemistry e.g. from J. March (1992), "Advanced Organic Chemistry: Reactions, Mechanisms, and Structure", 4$^{th}$ ed. John Wiley & Sons.

In the second step of the reaction the methyl hydroxy group of alcohol derivative of formula Ic is converted via a deoxygenation reaction to the corresponding methylene group to obtain compound of formula Id. The reaction is conveniently carried out in the presence of trialkylsilane such as trimethylsilane, triethylsilane or tripropylsilane, preferably triethylsilane, dissolved in mineral acids such as trifluoroacetic acid (TFA) or in Lewis acids such as $SnCl_4$ (described in D. L. Comins et al., Tet. Lett., 1986, 27, 1869), preferably with trifluoroacetic acid at a reaction temperature from 0° C. to 80° C., preferably at a reaction temperature between about 5° C. and about 50° C. Alternatively, the reduction reaction can also be carried in the presence P2I4 as described in EP 0627423.

For the synthesis of compounds of formula Ic or Id wherein the substituents are as defined above and $R^2$ is hydrogen, the corresponding compound of formula VI is N-protected as described for reaction scheme 1, further reacted according to reaction steps 4–5 of reaction scheme 1, then reacted according to reaction scheme 2 and finally deprotected as described for reaction scheme 1.

For the synthesis of compounds of formula Ic or Id wherein the substituents are as defined above and $R^1$ is hydrogen, compound of formula VIII wherein $R^1$ is a N-protecting group such as 4-methoxybenzyl (prepared according to reaction scheme 1) is reacted according reaction scheme 2 and finally deprotected as described for reaction scheme 1.

Optionally, compounds of formula Ic or Id wherein the substituents are as defined above and $R^1$ or $R^2$ is hydrogen and the other one of $R^1$ or $R^2$ is as defined above, can also be converted to the corresponding compound of formula Ic or Id wherein $R^1$, $R^2$, $R^3$, X and Z are as defined above. The reaction is carried out as described for reaction scheme 1.

Reaction scheme 3:

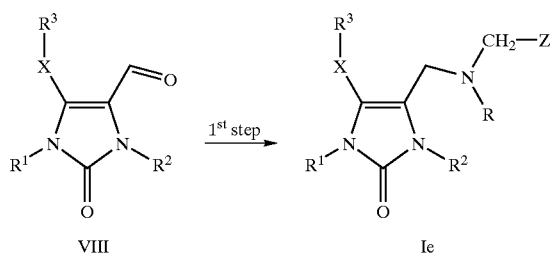

VIII                    Ie wherein R, $R^1$, $R^2$, $R^3$, X and Z are as defined for compounds of formula I.

In reaction scheme 3, the first reaction step is carried out in that aldehyde of formula VIII is derivatised via a reductive amination reaction with a primary or secondary amine of formula RN(H)CH$_2$—Z wherein R and Z are as defined for compounds of formula I to the corresponding amine compounds of formula Ie. The amines of formula RN(H)CH$_2$—Z are commercially available or can be synthesized according to known methods from textbooks on organic chemistry e.g. from J. March (1992), "Advanced Organic Chemistry: Reactions, Mechanisms and Structure", 4$^{th}$ ed. John Wiley and Sons. The reductive amination reaction is known from textbooks about organic chemistry e.g. from J. March (1992), "Advanced Organic Chemistry: Reactions, Mechanisms, and Structure", 4$^{th}$ ed. John Wiley & Sons. The reaction may be carried out in an inert solvent such as hydrocarbons for example cyclohexane, methyl cyclohexane, decaline, benzene, toluene, o-xylene, m-xylene or p-xylene, preferably toluene at a reaction temperature between about 60° C. and about boiling temperature of the organic solvent. After the reaction system has been cooled down, the organic solvent is evaporated and the residue is dissolved in an alcoholic solvent or ether for example methanol, ethanol, propanol, butanol, octanol or cyclohexanol, tetrahydrofuran, diethyl ether, dibutyl ether, dioxane or diglyme, preferably methanol, ethanol or tetrahydrofuran or a mixture of the mentioned solvents. The pH is adjusted in the range from 4.0 to 6.0, preferably in the range from 4.5 to 5.5 with inorganic acids, e.g. with hydrohalic acids such as hydrochloric acid, hydrobromic acid, sulphuric acid, nitric acid or phosphoric acid, and the like or with organic acids, e.g. with acetic acid, formic acid, tartaric acid, succinic acid, fumaric acid, maleic acid, malic acid, salicylic acid, citric acid, methanesulphonic acid and p-toluene sulphonic acid and the like. Subsequently, the system was reacted with a suitable reducing agent such as cyanoborohydride, sodium borohydride, NaBH$_4$, BH$_3$—THF, BH$_3$—SMe$_2$, catecholborane or other known in the art, preferably sodium cyanoborohydride or NaBH(OAc)$_3$ at a reaction temperature between about −10° C. and about 60° C., preferably at room temperature.

For the synthesis of compounds of formula Ie wherein the substituents are as defined above and $R^2$ is hydrogen, the corresponding compound of formula VI is N-protected with an appropriate protecting group as described for reaction scheme 1, further reacted according to reaction steps 4–5 of reaction scheme 1, then reacted according to reaction scheme 3 and finally deprotected as described for reaction scheme 1.

For the synthesis of compounds of formula Ie wherein the substituents are as defined above and $R^1$ is hydrogen, compound of formula VIII wherein $R^1$ is a N-protecting group such as 4-methoxybenzyl (prepared according to reaction scheme 1) is reacted according to reaction scheme 3 and finally deprotected as described for reaction scheme 1.

Optionally, compounds of formula Ie wherein the substituents are as defined for compounds of formula I and $R^1$ or $R^2$ is hydrogen and the other one of $R^1$ or $R^2$ is as defined for compounds of formula I, can also be converted to the corresponding compound of formula Ie wherein $R^1$, $R^2$, $R^3$, X and Z are as defined for compounds of formula I. The reaction is carried out as described for reaction scheme 1.

Reaction scheme 4:

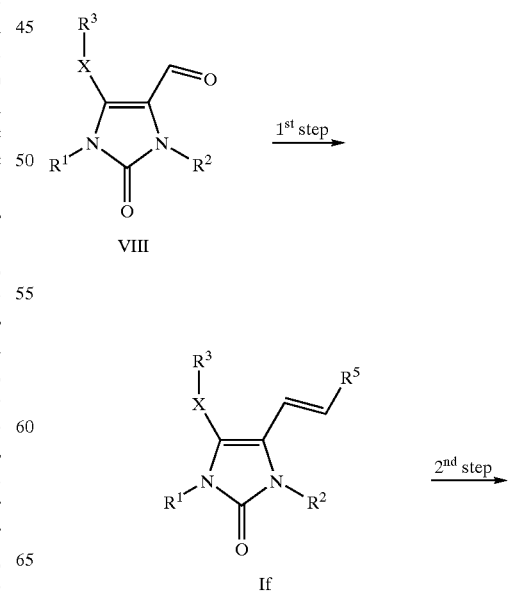

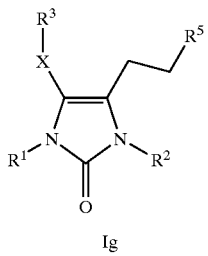

Ig wherein $R^1$, $R^2$, $R^3$ and X are as defined for compounds of formula I and $R^5$ is hydrogen, alkyl, protected hydroxy-$C_{0-2}$-alkyl or $C_{0-2}$-alkyl substituted with optionally substituted phenyl or with optionally substituted heterocyclyl as defined for compounds of formula I or $C_{0-2}$-alkyl substituted with $C_{1-4}$-alkoxy, $C_{1-4}$-alkyl-carbonyl-oxy- or heterocyclyl-oxy.

In reaction scheme 4, the first reaction step is carried out in that the aldehyde function of compound of formula VIII reacted via a Wittig-Horner reaction with dialkyl phosphonate of formula $(EtO)_2P(=O)(CH_2)R^5$ wherein $R^5$ is as defined above (commercially available or synthesised according to known methods from textbooks on organic chemistry e.g. from J. March (1992), "Advanced Organic Chemistry: Reactions, Mechanisms and Structure", 4th ed. John Wiley and Sons), to obtain olefinic compound of formula If. The reaction is carried out similar to the method described in the literature, for example in the presence of a strong base such as n-BuLi or preferably sodium hydride in an organic solvent for example anhydrous ethers such as diethyl ether, dibutyl ether, dioxane, preferably anhydrous tetrahydrofuran under inert atmosphere such as nitrogen or argon atmosphere at a reaction temperature from 0° C. to 80° C., preferably at a reaction temperature between about 5° C. and about 50° C. Optionally, olefinic compound of formula If can be obtained through other coupling reactions for example the Wittig reaction.

In the second step of the reaction, the olefinic group of compound of formula If is hydrogenated to the corresponding compound of formula Ig. The reaction is carried out similar to methods described in the literature, for example under hydrogen in the presence of a hydrogenation catalyst in an appropriate solvent at a reaction temperature from 0° C. to 80° C., preferably at a reaction temperature between about 5° C. and about 50° C. The hydrogen pressure can be between about 0 atm and about 100 atm, preferably between about 0 atm and about 50 atm and most preferred between about 0 atm and about 20 atm. The hydrogenation catalyst used for this reaction can be one of the commonly known catalysts such as noble metals (e.g. Pt, Pd or Rh) on supporting materials such as activated carbon or $Al_2O_3$, or generally as described in textbooks about organic chemistry e.g. J. March (1992), "Advanced Organic Chemistry: Reactions, Mechanisms, and Structure", 4th ed. John Wiley & Sons. Preferred hydrogenation catalysts are Pd on activated carbon or Raney-Nickel. Appropriate solvents for the hydrogenation reaction are organic solvents such as alcohols (e.g. methanol, ethanol, propanol, butanol, octanol or cyclohexanol), ethers (e.g. tetrahydrofuran, diethyl ether, dibutyl ether or dioxane), polar aprotic solvents such as dimethylsulfoxide (DMSO) or N,N-dimethylacetamide, esters (e.g. ethyl acetate), halogenated hydrocarbons (e.g. dichloromethane or trichloromethane), hydrocarbons (e.g. cyclohexane, methyl cyclohexane, decaline, benzene, toluene, o-xylene, m-xylene or p-xylene) or a mixtures of the mentioned solvents. Preferred solvents are ester, most preferred solvent is ethyl acetate.

For the synthesis of compounds of formula Ig wherein $R^5$ is unprotected hydroxy-$C_{0-2}$-alkyl, the protected hydroxy group of compound of formula Ig is deprotected according to methods known from the art for example as described in 'Protecting Groups in Organic Synthesis', second edition, Theodora W. Greene and Peter G. M. Wuts, Wiley-Interscience, 1991.

For the synthesis of compounds of formula Ig wherein the substituents are as defined above and $R^2$ is hydrogen, the corresponding compound of formula VI is N-protected with an appropriate protecting group as described for reaction scheme 1, further reacted according to reaction steps 4–5 of reaction scheme 1, then reacted according reaction scheme 4 and finally deprotected as described for reaction scheme 1.

For the synthesis of compounds of formula Ig wherein the substituents are as defined above and $R^1$ is hydrogen, compound of formula VIII wherein $R^1$ is a N-protecting group such as 4-methoxybenzyl (prepared according to reaction scheme 1) is reacted according to reaction scheme 4 and finally deprotected under conditions known from the literature for example under hydrogen in the presence of a catalyst such as palladium on charcoal or platinum on charcoal.

Optionally, compounds of formula Ig wherein the substituents are as defined above and $R^1$ or $R^2$ is hydrogen and the other one of $R^1$ or $R^2$ is as defined above, can also be converted to the corresponding compound of formula Ig wherein the substituents are as defined above. The reaction is carried out as described for reaction scheme 1.

Assay Method: HIV-1 Reverse Transcriptase Assay: Inhibitor $IC_{50}$ Determination HIV-1 RT assay was carried out in 96-well Millipore filtermat NOB50 plates using purified recombinant enzyme and a poly(rA)/oligo(dT)$_{16}$ template-primer in a total volume of 50 $\mu$L. The assay constituents were 50 mM Tris/HCl, 50 mM NaCl, 1 mM EDTA, 6 mM $MgCl_2$, 5 $\mu$M dTTP, 0.1 $\mu$Ci [$^3$H] dTTP, 5 $\mu$g/ml poly (rA) pre annealed to 2.5 $\mu$g/ml oligo (dT)$_{16}$ and a range of inhibitor concentrations in a final concentration of 10% DMSO. Reactions were initiated by adding 5 nM HIV-1 RT and after incubation at 37° C. for 30 min, they were stopped by the addition of 50 $\mu$l ice cold 20% TCA and allowed to precipitate at 4° C. for 30 min. The precipitates were collected by applying vacuum to the plate and sequentially washing with 2×200 $\mu$l of 10% TCA and 2×200 $\mu$l 70% ethanol. Finally the plates were dried and radioactivity counted in a Wallac Microbeta 1450 after the addition of 15 $\mu$l scintillation fluid per well. $IC_{50's}$ were calculated by plotting % inhibition versus log$_{10}$ inhibitor concentrations.

Antiviral Assay Method

Anti-HIV antiviral activity was assessed using an adaptation of the method of Pauwels et al. {Pauwels et al., 1988, J Virol Methods 20:309–321}. The method is based on the ability of compounds to protect HIV-infected T lymphoblastoid cells (MT4 cells) from cell-death mediated by the infection. The endpoint of the assay was calculated as the concentration of compound at which the cell viability of the culture was preserved by 50% ('50% inhibitory concentration', $IC_{50}$). The cell viability of a culture was determined by the uptake of soluble, yellow 3-[4,5-dimethylthiazol-2-yl]-2,5-diphenyltetrazolium bromide (MTT) and its reduction to a purple insoluble formazan salt. After solubilization, spectrophotometric methods were employed to measure the amount of formazan product.

MT4 cells were prepared to be in logarithmic-phase growth and a total of 2×10$^6$ cells infected with the HXB2-strain of HIV at a multiplicity of 0.0001 infectious units of virus per cell in a total volume of between 200–500 microlitres. The cells were incubated with virus for one h at 37° C. before removal of virus. The cells are then washed in 0.01 M phosphate buffered saline, pH 7.2 before being resuspensed in culture medium for incubation in culture with serial dilutions of test compound. The culture medium used was RPMI 1640 without phenol red, supplemented with penicillin, streptomycin, L-glutamine and 10% fetal calf serum (GM10).

Test compounds were prepared as 2 mM solutions in dimethyl sulphoxide (DMSO). Four replicate, serial 2-fold dilutions in GM10 were then prepared and 50 microlitres amounts placed in 96-well plates over a final nanomolar concentration range of 625–1.22. Fifty microlitres GM10 and $3.5 \times 10^4$ infected cells were then added to each well. Control cultures containing no cells (blank), uninfected cells (100% viability; 4 replicates) and infected cells without compound (total virus-mediated cell death; 4 replicates) were also prepared. The cultures were then incubated at 37° C. in a humidified atmosphere of 5% $CO_2$ in air for 5 s.

A fresh solution of 5 mg/ml MTT was prepared in 0.01 M phosphate buffered saline, pH 7.2 and 20 microlitres added to each culture. The cultures were further incubated as before for 2 h. They were then mixed by pipetting up and down and 170 microlitres of Triton X-100 in acidified isopropanol (10% v/v Triton X-100 in 1:250 mixture of concentrated HCl in isopropanol). When the formazan deposit was fully solubilized by further mixing, the absorbance (OD) of the cultures was measured at 540 nm and 690 nm wavelength (690 nm readings were used as blanks for artefacts between wells). The percent protection for each treated culture was then calculated from the equation:

$$\% \text{ Protection} = \frac{(\text{OD drug-treated cultures}) - (\text{OD untreated virus control cultures})}{(\text{OD uninfected cultures}) - (\text{OD untreated virus control cultures})} \times 100 \%$$

The $IC_{50}$ was then obtained from graph plots of percent protection versus $\log_{10}$ drug concentration.

In the assay, compounds of formulas I range in activity from an HIV $IC_{50}$ of about 0.5 to about 5000 nM, with preferred compounds having a range of activity from about 0.5 to about 750 nM, more preferably about 0.5 to 300 nM, and most preferably about 0.5 to 50 nM.

| Structure | RT $IC_{50}$ [nM] | HIV $IC_{50}$ [nM] |
|---|---|---|
| | 90 | 7 |
| 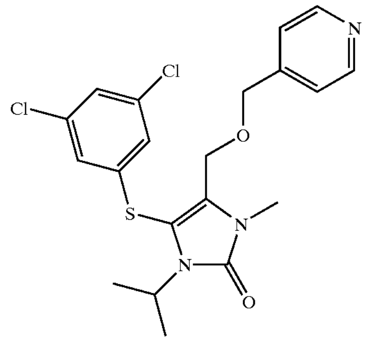 | 171 | 4 |
| 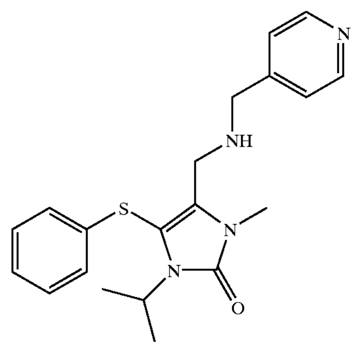 | 520 | 32 |
| 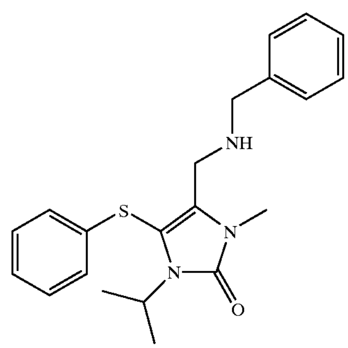 | 730 | 44 |
| 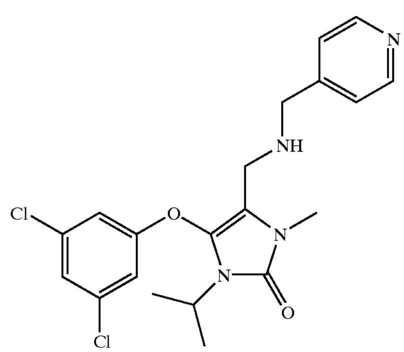 | 2400 | 108 |

-continued

| Structure | RT IC$_{50}$ [nM] | HIV IC$_{50}$ [nM] |
|---|---|---|
| (structure) | 1160 | ND |
| (structure) | 1905 | ND |
| (structure) | 3339 | ND |
| (structure) | 10000 | ND |

-continued

| Structure | RT IC$_{50}$ [nM] | HIV IC$_{50}$ [nM] |
|---|---|---|
| (structure) | 10000 | ND |
| (structure) | 1919 | ND |
| (structure) | 649 | ND |
| (structure) | 313 | 7 |
| (structure) | 608 | 134 |

| Structure | RT IC$_{50}$ [nM] | HIV IC$_{50}$ [nM] |
|---|---|---|
| (structure) | 115 | 5 |

ND: not determined

The imidazolone derivatives provided by the present invention can be used together with a therapeutically inert carrier as medicaments in the form of pharmaceutical preparations. The pharmaceutical preparations can be administered enterally, such as orally, in the form of tablets, coated tablets, dragées, hard and soft gelatine capsules, solutions, emulsions or suspensions, or nasally, e.g. in the form of nasal sprays. They can also be administered rectally, e.g. in the form of suppositories, or parenterally, (e.g. intramuscularly, intravenously, or subcutaneously), for example, in the form of injection solutions.

For the manufacture of pharmaceutical preparations the imidazolone derivatives can be formulated with therapeutically inert, inorganic or organic carriers.

Lactose, corn starch or derivatives thereof, talc, stearic acid or its salts can be used, for example, as such carriers for tablets, coated tablets, dragées and hard gelatine capsules.

Suitable carriers for soft gelatine capsules are, for example, vegetable oils, waxes, fats, semi-solid and liquid polyols and the like.

Suitable carriers for the manufacture of injection solutions are, for example, water, saline, alcohols, polyols, glycerine, vegetable oils and the like. Natural or hardened oils, waxes, fats, semi-liquid or liquid polyols and the like are suitable carriers for the manufacture of suppositories. The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants.

The pharmaceutical preparations may also contain other therapeutically active agents such as those mentioned above.

The imidazolone derivatives provided by the invention in the treatment of an immune mediated condition or disease, a viral disease, a bacterial disease, a parasitic disease, an inflammatory disease, a hyperproliferative vascular disease, a tumor, or cancer.

The dosage can vary within wide limits and will, of course, be adjusted to the individual requirements in each particular case.

Dosage levels of between about 0.01 and about 100 mg/kg body weight per day in monotherapy and/or in combination therapy are commonly administered from about 1 to 5 times per day. A typical preparation will contain from about 5% to 95% active compound (w/w). The daily dosage can be administered as a single dosage or in divided dosages.

The imidazolone derivatives provided by the present invention or the medicaments thereof may be for use in monotherapy and/or combination therapy, i.e. the treatment may be in conjunction with the administration of one or more additional therapeutically active substance(s). When the treatment is combination therapy, such administration may be concurrent or sequential with respect to that of the imidazolone derivatives of the present invention. Thus, concurrent administration, as used herein, includes administration of the agents in conjunction or combination, together, or before or after each other.

It will be understood that references herein to treatment extend to prophylaxis as well as to treatment of existing conditions. Treatment of a disease or condition, as used herein, also includes preventing, inhibiting, regressing, reversing, alleviating or relieving the disease or condition, or the clinical symptoms thereof. The term "subject" as used herein refers to animals, including humans and other mammals.

In the following examples the abbreviations used have the following significations:

| | |
|---|---|
| MS | mass spectroscopy |
| ES | electrospray |
| EI | electron impact |
| NMR | nuclear magnetic resonance spectroscopy |
| DMF | N,N-dimethylformamide |
| DMSO | dimethylsulfoxide |
| rt | room temperature |
| min | minute(s) |
| h | hour(s) |
| d | day(s) |

All temperatures are given in degrees Celsius (° C.).

The described NMR spectra were recorded on a Bruker DRX 400 MHz spectrometer with the probe temperature set at 300 K.

The mass spectra indicated by "(M+; EI)", were recorded under electron impact conditions (EI), on a THERMO-QUEST MAT95 S with a source temperature of 200° C. Other mass spectra were recorded under electrospray ionization spectra (ESI) conditions, on one of the following machines:

a) THERMOQUEST SSQ 7000 [Solvent 0.085% TFA in 90% Acetonitrile/water; flow rate 100 microliters/minute; capillary 250° C.; spray voltage 5 KV; sheath gas 80 psi], or b) LC-MS system (liquid chromatograph coupled to mass spectrum) THERMOQUEST TSQ 7000 ELECTRO-SPRAY or MICROMASS PLATFORM ELECTRO-SPRAY [Solvent 0.1% TFA in water or 0.085% TFA in 90% acetonitrile/ water or 0.085% TFA in acetonitrile].

With regard to the starting materials that are known compounds some of these may be purchased from commercial suppliers. Other starting materials that are known and their analogues can be prepared by methods well known in the art. Examples of compounds available from commercial suppliers, and citations to the synthesis of other compounds and their analogues are provided in the following: Compounds, whenever prepared by the processes of the present invention are also an object of the present invention.

The following examples illustrate the present invention:

EXAMPLE 1

4-(3,5-Dichlorophenylthio)-5-(hydroxymethyl)-3-isopropyl-1-methyl-1,3-dihydro-2-imidazolone A mixture of 117 mg of 5-(3,5-dichlorophenylthio)-1-isopropyl-3-methyl-1,3-dihydro-2-imidazolone-4- carboxaldehyde and 33 mg of sodium borohydride in 4 ml of tetrahydrofuran and 1 ml of ethanol was stirred at rt for 3 h. The reaction mixture was reduced in volume and the residue was purified by flash chromatography on silica gel using ethyl acetate/hexane (1:1 then 2:1 then 100% ethyl acetate) for the elution to give 113 mg of white crystals. Mass spectrum (ES) m/z 347 [M+H]$^+$.

The starting material was prepared as follows:

Intermediate 1A 5-(3,5-dichlorophenylthio)-1-isopropyl-3-methyl-1, 3-dihydro-2-imidazolone-4-carboxaldehyde To a solution of 4.16 g of 5-chloro-1-isopropyl-3-methyl-1,3-dihydro-2-imidazolone-4-carboxaldehyde in 50 ml of dichloromethane was added 4.4 g of 3,5-dichlorothiophenol and 6.8 ml of triethylamine. The mixture was stirred at rt under nitrogen for 18 h. The reaction mixture was concentrated and partitioned between ethyl acetate and 2N hydrochloric acid. The organic layer was washed with a further aliquot of 2N hydrochloric acid and brine then dried, filtered and evaporated to dryness. The residue crystallised on standing to provide a solid, which was triturated with diethyl ether to give 5 g of a white solid. Mass spectrum (ES) m/z 344 [M+H]$^+$.

Intermediate 1B

5-Chloro-1-isopropyl-3-methyl-1,3-dihydro-2-imidazolone-4-carboxaldehyde

A solution of 6.5 g of 5-dimethylaminomethylene-3-isopropyl-1-methyl-imidazolidine-2,4-dione in 30 ml of phosphorus oxychloride and 5 ml of dimethylformamide was heated to 100° C. for 2 h. After this time, the reaction mixture was cooled to rt, poured into ice water and extracted with ethyl acetate. The organic extract was dried, filtered and evaporated to give 4.16 g as yellow needles. Mass spectrum (EI) m/z 202 M$^+$.

Intermediate 1C

5-Dimethylaminomethylene-3-isopropyl-1-methyl-imidazolidine-2,4-dione

A mixture of 13.4 g of 3-isopropyl-1-methyl-imidazolidine-2,4-dione and 13.6 ml dimethylformamide dimethylacetal were heated at 100° C. over the weekend. The reaction mixture was cooled to rt and purified by flash chromatography to give 9.9 g of a golden oil. Mass spectrum (EI) m/z 211 M$^+$.

Intermediate 1D

3-Isopropyl-1-methylimidazolidine-2,4-dione

A mixture of 14.9 g of (3-isopropyl-1-methylureido)acetic acid in 50 ml of water and 50 ml of concentrated hydrochloric acid was refluxed for 2 h. On cooling the mixture was diluted with water and extracted with ethyl acetate to give 13.4 g of a colourless oil. Mass spectrum (EI) m/z 156 M$^+$.

Intermediate 1E (3-Isopropyl-1-methylureido)acetic acid

To a solution of 4 g of sodium hydroxide in 75 ml of water was added 10 g of sarcosine portionwise. The solution was cooled and treated with 11.5 ml of isopropyl isocyanate. After 2 h, the reaction mixture was washed with diethyl ether and the aqueous phase acidified with concentrated HCl to <pH 2. The product was extracted twice with ethyl acetate to give 10.45 g of a white solid which was taken on to the next step.

A further extraction of the aqueous phase after standing gave 5.5 g of a colourless oil the next product.

EXAMPLE 2

5-(Benzyloxymethyl)-4-(3,5-dichlorophenylthio)-3-isopropyl-1-methyl-1,3-dihydro-2-imidazolone To 50 mg of 4-(3,5-dichlorophenylthio)-5-(hydroxymethyl)-3-isopropyl-1-methyl-1,3-dihydro-2-imidazolone in 1 ml of dimethylformamide was added 7 mg of sodium hydride (60% dispersion in oil). The reaction mixture was stirred at rt for 30 min until hydrogen gas evolution had ceased. The solution was then treated with 20 μL of benzyl bromide and stirring continued for 1 h. The reaction mixture was partitioned between ethyl acetate and water. The organic layer was separated, dried and evaporated to dryness to give 190 mg of an oily residue. This residue was purified by flash chromatography on silica gel using ethyl acetate/hexane (1:1) for the elution to give 55 mg of a colourless oil. Mass spectrum (ESI) m/z 437 [M+H]$^+$.

EXAMPLE 3

5-(Benzyloxymethyl)-4-(3,5-dichlorophenoxy)-3-isopropyl-1-methyl-1,3-dihydro-2-imidazolone To 115 mg of 4-(3,5-dichlorophenoxy)-5-hydroxymethyl-3-isopropyl-1-methyl-1,3-dihydro-2-imidazolone in 5 ml of dimethylformamide was added 15 mg of sodium hydride (60% dispersion in oil). The reaction mixture was stirred at rt for 30 min until hydrogen gas evolution had ceased. The solution was then treated with 45 μL of benzyl bromide and stirring continued for 1 h. The reaction mixture was partitioned between ethyl acetate and water. The organic layer was separated, dried and evaporated to dryness to give 190 mg of an oily residue. This residue was purified by flash chromatography on silica gel using ethyl acetate/hexane (1:1) for the elution to give 41 mg of a colourless oil. Mass spectrum (ESI) m/z 421 [M+H]$^+$.

The starting material was prepared as follows:

EXAMPLE 3A 4-(3,5-Dichlorophenoxy)-5-hydroxymethyl-3-isopropyl-1-methyl-1,3-dihydro-2-imidazolone A mixture of 100 mg of 5-(3,5-dichlorophenoxy)-1-isopropyl-3-methyl-1,3-dihydro-2-imidazolone-4-carboxaldehyde and 13 mg of sodium borohydride in 5 ml of methanol was stirred at rt for 2 h. The reaction mixture was reduced in volume then dissolved in ethyl acetate. The solution was washed with water, dried and evaporated to dryness to give 115 mg of colourless needles. Mass spectrum (ESI) m/z 331 [M+H]$^+$.

EXAMPLE 3B 5-(3,5-Dichlorophenoxy)-1-isopropyl-3-methyl-2,3-dihydro-2-imidazolone-4-carboxaldehyde To a solution of 163 mg of 3,5-dichlorophenol in 3 ml of dimethylformamide was added portionwise 26 mg of sodium hydride (as a 60% dispersion in mineral oil). The reaction mixture was stirred until evolution of hydrogen gas has ceased then was treated with 200 mg of 5-chloro-1-isopropyl-3-methyl-1,3-dihydro-2-imidazolone-4-carboxaldehyde. The mixture was stirred overnight at rt. The reaction mixture was diluted with ethyl acetate and washed with dilute sodium hydroxide solution. The organic phase was dried, filtered and evaporated to give 341 mg of a buff solid. Mass spectrum (ESI) m/z 437, 438 [M+H]$^+$.

EXAMPLE 4

4-(3,5-Dichlorophenylthio)-5-(hydroxymethyl)-3-isopropyl-1-(4-methoxybenzyl)-1,3-dihydro-2-imidazolone A mixture of 50 mg of 5-(3,5-dichlorophenylthio)-1-isopropyl-3-(4-methoxybenzyl)-1,3-dihydro-2-imidazolone-4-carboxaldehyde and 5 mg of sodium borohydride in 5 ml of methanol was stirred at rt for 2 h. The reaction mixture was reduced in volume and dissolved in ethyl acetate, washed with water, dried and evaporated to give 50 mg of a white solid. Mass spectrum (ESI) m/z 453 [M+H]$^+$.

The starting material was prepared as follows:

Intermediate 4A

5-(3,5-Dichlorophenylthio)-1-isopropyl-3-(4-methoxybenzyl)-1,3-dihydro-2-imidazolone-4-carboxaldehyde To a solution of 1.99 g of 5-chloro-1-isopropyl-3-(4-methoxybenzyl)-1,3-dihydro-2-imidazolone-4-carbaldehyde in 25 ml of dichloromethane was added 1.2 g of 3,5-dichlorothiophenol and 2 ml of triethylamine. The mixture was stirred at rt under nitrogen for 18 h. The reaction mixture was concentrated and partitioned between ethyl acetate and 2N hydrochloric acid. The organic layer was washed with a further aliquot of 2N hydrochloric acid and brine then dried, filtered and evaporated to dryness. The residue crystallised on standing to provide a solid, which was triturated with diethyl ether to give 1.4 g of a white solid. Mass spectrum (ESI) m/z 451 [M+H]$^+$.

Intermediate 4B

5-Chloro-1-isopropyl-3-(4-methoxybenzyl)-13-dihydro-2-imidazolone-4-carboxaldehyde A mixture of 1.99 g of 5-dimethylaminomethylene-3-isopropyl-1-(4-methoxybenzyl)imidazolidine-2,4-dione 10 ml of phosphorus oxychloride and 2 ml of dimethylformamide was heated at 100° C. for 2 h. The reaction mixture was cooled to rt, poured onto ice water and extracted with ethyl acetate. After evaporation the crude product was purified by flash chromatography to give 2.2 g of an oil. Mass spectrum (ESI) m/z 309 [M+H]$^+$.

Intermediate 4C

5-Dimethylaminomethylene-3-isopropyl-1-(4-methoxybenzyl)-imidazolidine-2,4-dione To a solution of 100 mg of 5-dimethylaminomethylene-3-isopropylimidazolidine-2,4-dione in 2 ml of dimethylformamide was added 425 mg of sodium hydride (as a 60% dispersion in mineral oil). The mixture was stirred until evolution of hydrogen gas had ceased. The solution was then treated with 1.5 ml of 4-methoxybenzyl chloride and stirring continued overnight at rt. The mixture was partitioned between ethyl acetate and water and the organic layer dried, filtered and concentrated. The residue was purified by flash chromatography eluting with 1:1 ethyl acetate: haxane to give 85 mg of a colourless oil. $^1$H NMR (400 MHz, deuteriochloroform): δ=1.40 (6H, d, J=7 Hz), 3.02 (6H, s), 3.72 (3H, s), 4.38 (1H, septet, J=7 Hz), 4.60 (2H, s), 5.96 (1H, s), 6.80 (2H, d, J=8 Hz), 7.05 (2H, d, J=8 Hz).

Intermediate 4D

5-Dimethylaminomethylene-3-isopropylimidazolidine-2,4-dione

A mixture of 5 g of 3-isopropylimidazolidine-2,4-dione and 5 ml dimethylformamide dimethylacetal were heated at 100° C. for 3 s. The reaction mixture was cooled to rt and purified by flash chromatography to give 2 g of an orange solid. $^1$H NMR (400 MHz, deuteriochloroform): δ=1.42 (6H, d, J=7 Hz), 3.11 (6H, s), 4.40 (1H, septet, J=7 Hz), 6.64 (1H, s), 9.55 (1H, br s).

Intermediate 4E

3-Isopropylimidazolidine-2,4-dione

To a solution of 3.6 g of sodium hydroxide in 75 ml of water was added 7.5 g of glycine. The solution was cooled to 5° C. and treated with 9.8 ml of isopropylisocyanate. After 5 h the reaction mixture was neutralised with 50 ml concentrated hydrochloric acid added dropwise to the slurry. This mixture was refluxed for 2 h then cooled to rt. The product was extracted with ethyl acetate to give 10.9 g of a colourless oil. $^1$H NMR (400 MHz, deuteriochloroform): δ=1.45 (6H, d, J=7 Hz), 3.92 (2H, s), 4.35 (1H, septet, J=7 Hz), 6.39 (1H, br s).

EXAMPLE 5

4-(3,5-Dichlorophenylthio)-5-(2-hydroxybenzyl)-3-isopropyl-1-methyl-1,3-dihydro -2-imidazolone To a solution of 100 mg of 4-(3,5-dichlorophenylthio)-5-(hydroxymethyl)-3-isopropyl-1-methyl-1,3-dihydro-2-imidazolone, 30 mg of phenol and 100 mg of triphenylphosphine in 5 mL of tetrahydrofuran at 0° C. was added 70 μL of diisopropylazodicarboxylate in 5 mL of tetrahydrofuran over 20 min. The reaction was stirred overnight warming to room temperature. The mixture was then diluted with ethyl acetate and washed with 0.5N hydrochloric acid solution then 0.5N sodium hydroxide solution, dried, concentrated and purified by flash chromatography eluting with 3:1 hexane: ethyl acetate to give 16 mg of a colourless oil. Mass spectrum (ES) m/z 423 [M+H]$^+$.

EXAMPLES 6–9 and 33–39

The compounds shown in table 2 were prepared in a manner analogous to that described for examples 1 to 5:

TABLE 2

| Ex. | Structure | Name | MS (ES) (M + H)+ |
|---|---|---|---|
| 6 | 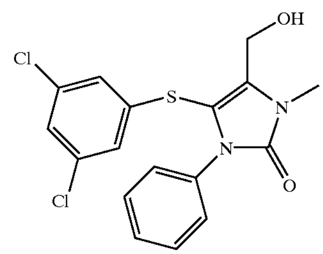 | 4-(3,5-Dichlorophenylthio)-5-hydroxymethyl-1-methyl-3-phenyl-1,3-dihydro-2-imidazolone | 382 |
| 7 | 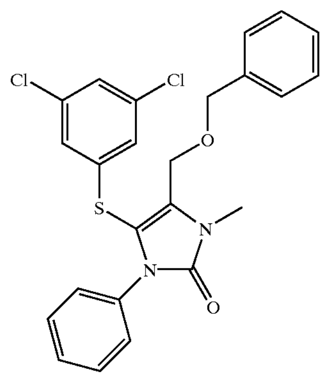 | 5-Benzyloxymethyl-4-(3,5-dichlorophenylthio)-1-methyl-3-phenyl-1,3-dihydro-2-imidazolone | 471 |
| 8 | 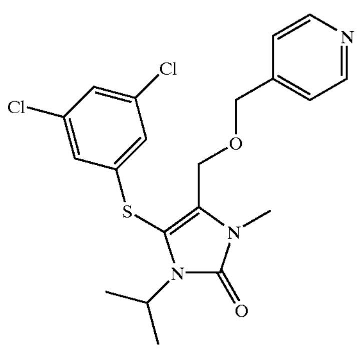 | 4-(3,5-Dichlorophenylthio)-3-isopropyl-1-methyl-5-(pyridin-4-ylmethoxymethyl)-1,3-dihydro-2-imidazolone | 438 |
| 9 | 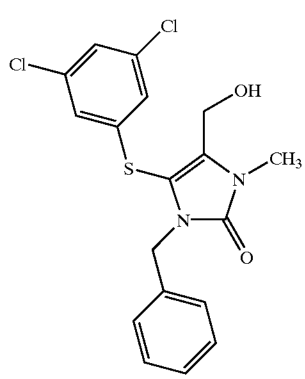 | 3-Benzyl-4-(3,5-dichlorophenylthio)-5-hydroxymethyl-1-methyl-1,3-dihydro-2-imidazolone | 395 |

TABLE 2-continued

| Ex. | Structure | Name | MS (ES) (M + H)+ |
|---|---|---|---|
| 33 | 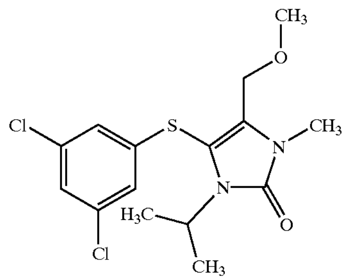 | 4-(3,5-Dichloro-phenylsulfanyl)-3-isopropyl-5-methoxymethyl-1-methyl-1,3-dihydro-imidazol-2-one | 362 |
| 34 | 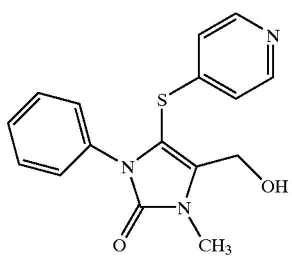 | 4-Hydroxymethyl-3-methyl-1-phenyl-5-(pyridin-4-ylsulfanyl)-1,3-dihydro-imidazol-2-one | 314 |
| 35 | 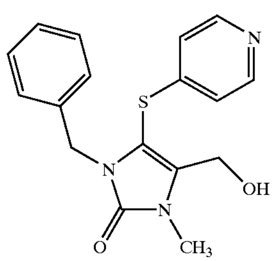 | 1-Benzyl-4-hydroxymethyl-3-methyl-5-(pyridin-4-ylsulfanyl)-1,3-dihydro-imidazol-2-one; hydrochloric acid | 364 |
| 36 | 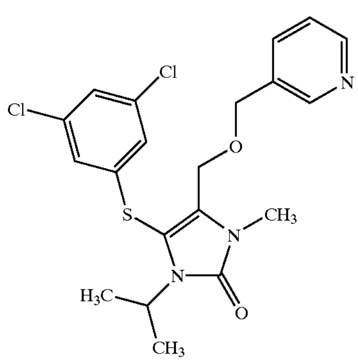 | 4-(3,5-Dichloro-phenylsulfanyl)-3-isopropyl-1-methyl-5-(pyridin-3-ylmethoxymethyl)-1,3-dihydro-imidazol-2-one | 439 |

TABLE 2-continued

| Ex. | Structure | Name | MS (ES) (M + H)+ |
|---|---|---|---|
| 37 | 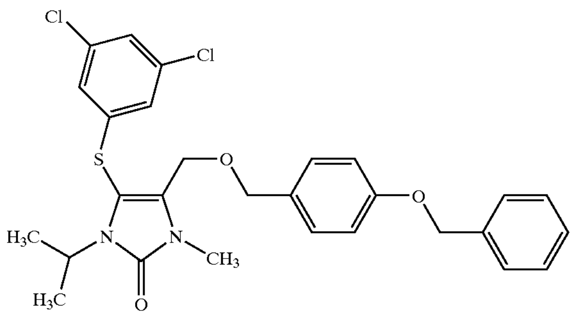 | 4-(4-Benzyloxy-benzyloxymethyl)-5-(3,5-dichloro-phenylsulfanyl)-1-isopropyl-3-methyl-1,3-dihydro-imidazol-2-one | 544 |
| 38 | 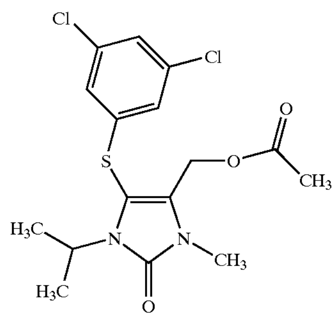 | Acetic acid 5-(3,5-dichloro-phenylsulfanyl)-1-isopropyl-3-methyl-2-oxo-2,3-dihydro-1H-imidazol-4-ylmethyl ester | 390 |
| 39 | 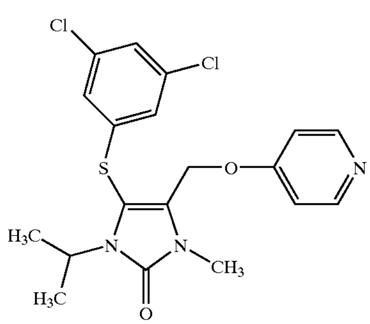 | 4-(3,5-Dichloro-phenylsulfanyl)-3-isopropyl-1-methyl-5-(pyridin-4-yloxymethyl)-1,3-dihydro-imidazol-2-one | 425 |

EXAMPLE 10

4-(3,5-Dichlorophenylthio)-5-(alpha(RS)-hydroxybenzyl)-3-isopropyl-1-methyl-1,3-dihydro-2-imidazolone A mixture of 345 mg of 5-(3,5-dichlorophenoxy)-1-isopropyl-3-methyl-1,3-dihydro-2-imidazolone-4-carboxaldehyde in 5 ml of tetrahydrofuran was added to 0.4 ml of a 3M solution of phenyl magnesium bromide also in 5 ml of tetrahydrofuran under nitrogen. The reaction was stirred at rt for 2 h then quenched with saturated ammonium chloride solution and extracted with ethyl acetate. The organic phase was washed with brine, dried and evaporated to give 490 mg of a solid foam. Mass spectrum (ESI) m/z 423 [M+H]+.

EXAMPLE 11

4-(3,5-Dichlorophenylthio)-3-isopropyl-1-methyl-5-benzyl-1,3-dihydro-2-imidazolone To a mixture of 250 mg of 4-(3,5-dichlorophenoxy)-5-(alpha(RS)-hydroxybenzyl)-3-isopropyl-1-methyl-1,3-dihydro-2-imidazolone in 3 ml of trifluoroacetic acid was added 90 μL of triethylsilane and stirred under nitrogen for 0.5 h. The reaction mixture was evaporated then the residue was purified by flash chromatography to give 245 mg of an amber oil. Mass spectrum (ES) m/z 407 [M+H]+.

EXAMPLES 12 and 40–48

The compounds shown in table 3 were prepared in a manner analogous to that described for examples 10 to 11:

TABLE 3

| Ex. | Structure | Name | MS (ES) (M + H)+ |
|---|---|---|---|
| 12 | 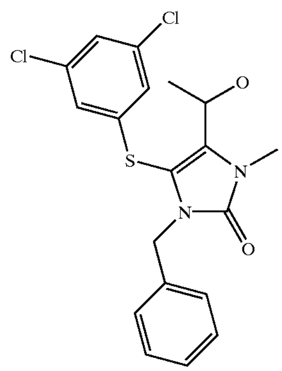 | 3-Benzyl-4-(3,5-dichlorophenylthio)-5-(1-hydroxyethyl)-1-methyl-1,3-dihydro-2-imidazolone | 409 |
| 40 | 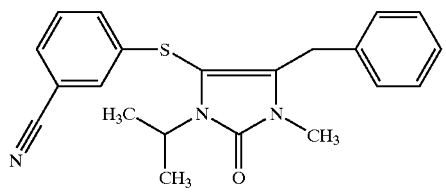 | 3-(5-Benzyl-3-isopropyl-1-methyl-2-oxo-2,3-dihydro-1H-imidazol-4-ylsulfanyl)-benzonitrile | 364 |
| 41 | 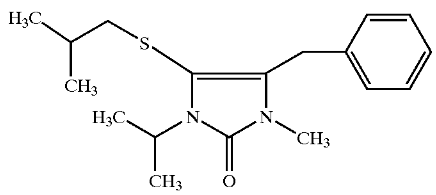 | 4-Benzyl-5-isobutylsulfanyl-1-isopropyl-3-methyl-1,3-dihydro-imidazol-2-one | 319 |
| 42 | 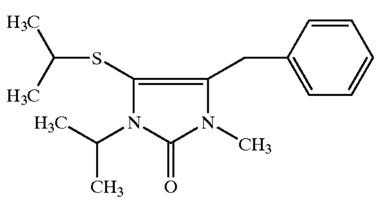 | 4-Benzyl-1-isopropyl-5-isopropylsulfanyl-3-methyl-1,3-dihydro-imidazol-2-one | 305 |
| 43 | 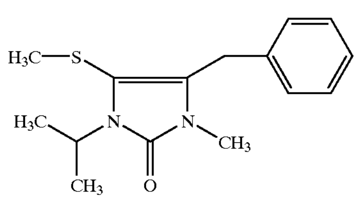 | 4-Benzyl-1-isopropyl-3-methyl-5-methylsulfanyl-1,3-dihydro-imidazol-2-one | 277 |
| 44 | 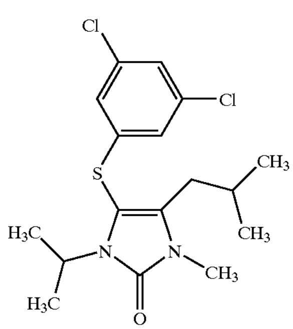 | 4-(3,5-Dichloro-phenylsulfanyl)-5-isobutyl-3-isopropyl-1-methyl-1,3-dihydro-imidazol-2-one | 374 |

TABLE 3-continued

| Ex. | Structure | Name | MS (ES) (M + H)+ |
|---|---|---|---|
| 45 | 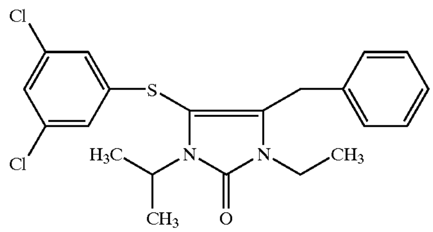 | 4-Benzyl-5-(3,5-dichloro-phenylsulfanyl)-3-ethyl-1-isopropyl-1,3-dihydro-imidazol-2-one | 422 |
| 46 | 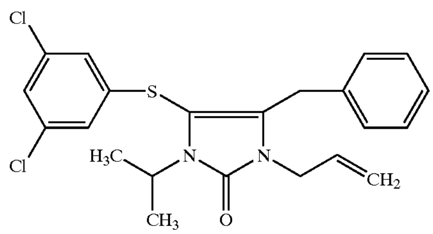 | 1-Allyl-5-benzyl-4-(3,5-dichloro-phenylsulfanyl)-3-isopropyl-1,3-dihydro-imidazol-2-one | 434 |
| 47 | 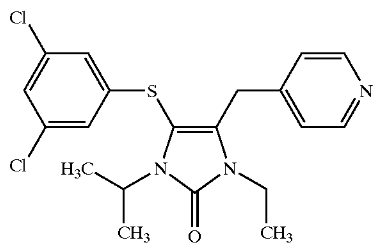 | 4-(3,5-Dichloro-phenylsulfanyl)-1-ethyl-3-isopropyl-5-pyridin-4-ylmethyl-1,3-dihydro-imidazol-2-one | 423 |
| 48 | 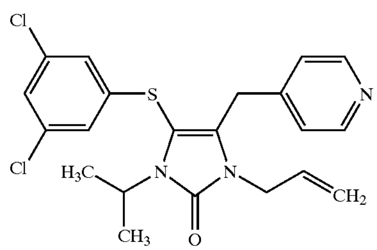 | 1-Allyl-4-(3,5-dichloro-phenylsulfanyl)-3-isopropyl-5-pyridin-4-ylmethyl-1,3-dihydro-imidazol-2-one | 435 |

EXAMPLE 13

4-(3,5-Dichlorophenylthio)-3-isopropyl-1-methyl-5-[[(4-pyridyl)methylamino]methyl]-1,3-dihydro-2-imidazolone A mixture of 100 mg of 4-(3,5-dichlorophenylthio)-1-isopropyl-3-methyl-1,3-dihydro-2-imidazolone-4-carboxaldehyde and 34 µL of 4-pyridylmethylamine in 10 ml of toluene was azeotroped in a Dean-Stark apparatus for 2 h. The reaction was cooled to rt, evaporated and re-dissolved in 10 ml of methanol. Bromocresol green was added and the pH adjusted to approximately 5 using 4N hydrochloric acid/dioxane. The solution was treated portionwise with 30 mg of sodium cyanoborohydride and the pH adjusted back to 5 using 4N hydrochloric acid/dioxane. This was repeated until the addition was complete. The reaction was evaporated and the residue was purified by flash chromatography on silica gel using ethyl acetate/hexane (2:1) followed by methanol/dichloromethane (1:19) for the elution to give 72 mg of a colourless oil. Mass spectrum (ES) m/z 437,438 [M+H]$^+$.

EXAMPLE 14

4-(3,5-Dichlorophenylthio)-3-isopropyl-1-(4-methoxybenzyl)-5-[[(4-pyridyl)methylamino]methyl]-1,3-dihydro-2-imidazolone A mixture of 1 g of 5-(3,5-dichlorophenylthio)-1-isopropyl-3-(4-methoxybenzyl)-dihydro-2-imidazolone-4-carboxaldehyde and 0.25 ml of 4-pyridylmethylamine in 20 ml of toluene was refluxed in a Dean-Stark apparatus for 2 h. The reaction was cooled to rt, evaporated and re-dissolved in 10 ml of methanol. Bromocresol green was added and the pH adjusted to approximately 5 using 4N hydrochloric acid/dioxane. The solution was treated portionwise with 155 mg of sodium cyanoborohydride and the pH adjusted back to 5 using 4N hydrochloric acid/dioxane. This was repeated until the addition was complete. The reaction was evaporated and the residue was purified by flash chromatography on silica gel eluting with ethyl acetate/hexane (2:1) followed by methanol/dichloromethane (1:19) to give 1.07 g of a golden solid. Mass spectrum (ES) m/z 543 [M+H]$^+$.

EXAMPLES 15–31

The compounds shown in table 4 were prepared in a manner analogous to that described for examples 13 to 14:

TABLE 4

| Ex. | Structure | Name | MS (ES) (M + H)+ |
|---|---|---|---|
| 15 | 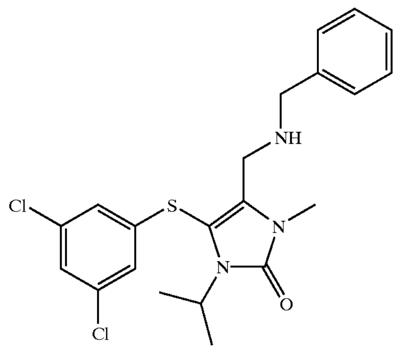 | 5-(Benzylaminomethyl)-4-(3,5-dichlorophenylthio)-3-isopropyl-1-methyl-1,3-dihydro-2-imidazolone | 477 ((M + MeCN + H)+; ESI) |
| 16 | 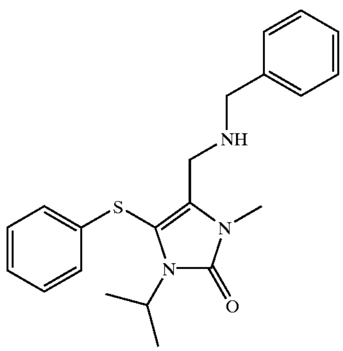 | 5-(Benzylaminomethyl)-3-isopropyl-1-methyl-4-phenylthio-1,3-dihydro-2-imidazolone | 367 |
| 17 | 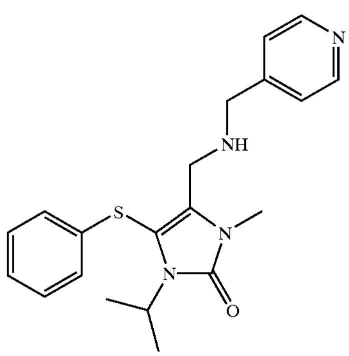 | 3-Isopropyl-1-methyl-4-phenylthio-5-{[(pyridin-4-ylmethyl)amino]methyl}-1,3-dihydro-2-imidazolone | 369 |
| 18 | 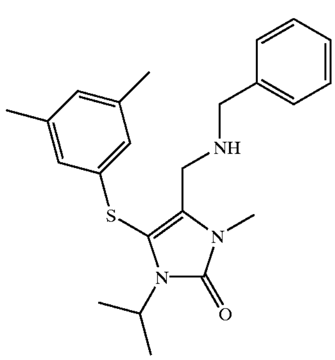 | 5-(Benzylaminomethyl)-4-(3,5-dimethylphenylthio)-3-isopropyl-1-methyl-1,3-dihydro-2-imidazolone | 396 |

TABLE 4-continued

| Ex. | Structure | Name | MS (ES) (M + H)+ |
|---|---|---|---|
| 19 | 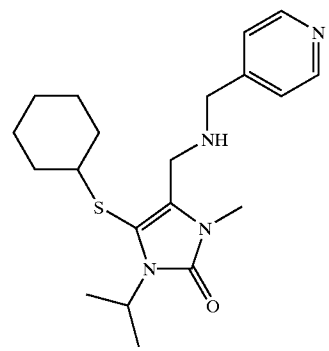 | 4-Cyclohexylthio-3-isopropyl-1-methyl-5-{[(pyridin-4-ylmethyl)amino]methyl}-1,3-dihydro-2-imidazolone | 375 |
| 20 | 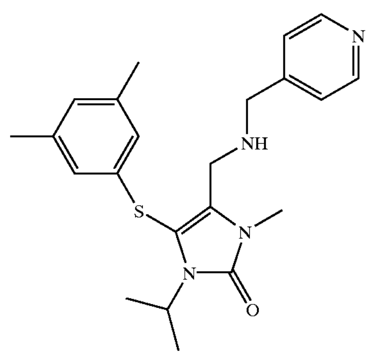 | 4-(3,5-Dimethylphenythio)-3-isopropyl-1-methyl-5-{[(pyridin-4-ylmethyl)amino]methyl}-1,3-dihydro-2-imidazolone | 397 |
| 21 | 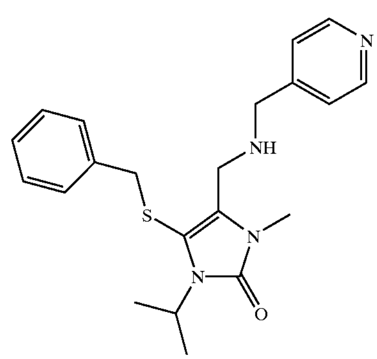 | 4-Benzylthio-3-isopropyl-1-methyl-5-{[(pyridin-4-ylmethyl)amino]methyl}-1,3-dihydro-2-imidazolone | 383 |
| 22 | 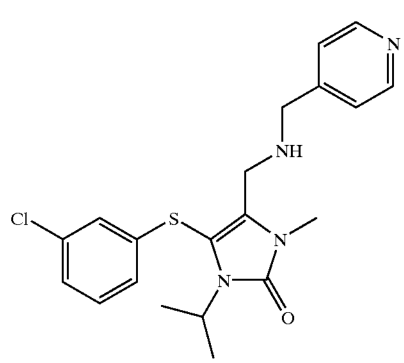 | 4-(3-Chlorophenylthio)-3-isopropyl-1-methyl-5-{[(pyridin-4-ylmethyl)amino]methyl}-1,3-dihydro-2-imidazolone | 403 |

TABLE 4-continued

| Ex. | Structure | Name | MS (ES) (M + H)+ |
|---|---|---|---|
| 23 | 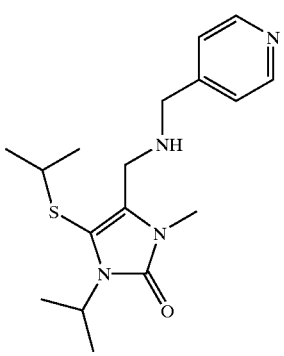 | 3-Isopropyl-4-isopropylthio-1-methyl-5-{[(pyridin-4-ylmethyl)amino]methyl}-1,3-dihydro-2-imidazolone | 355 |
| 24 | 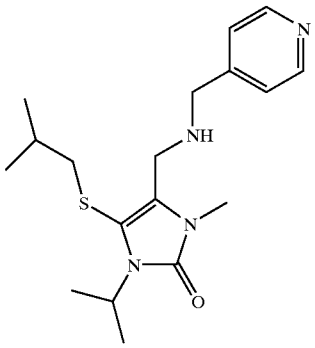 | 4-Isobutylthio-3-isopropyl-1-methyl-5-{[(pyridin-4-ylmethyl)amino]methyl}-1,3-dihydro-2-imidazolone | 349 |
| 25 | 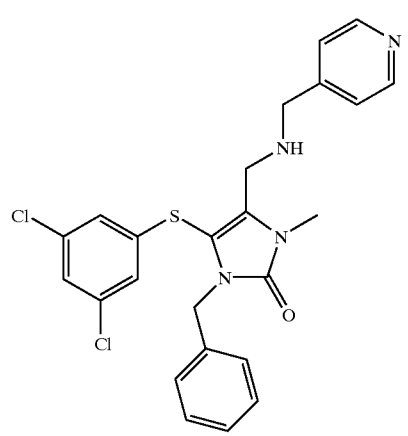 | 3-Benzyl-4-(3,5-dichlorophenylthio)-1-methyl-5-{[(pyridin-4-ylmethyl)amino]methyl}-1)3-dihydro-2-imidazolone | 485 |
| 26 | 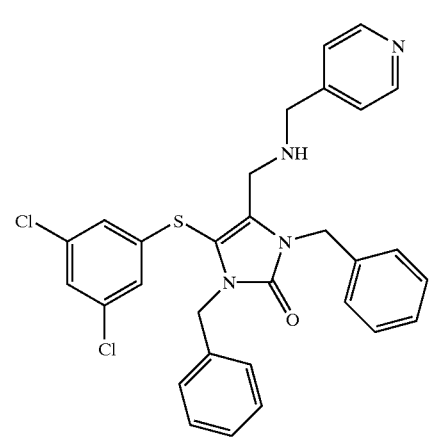 | 1,3-Dibenzyl-4-(3,5-dichlorophenylthio)-5-{[(pyridin-4-ylmethyl)amino]methyl}-1)3-dihydro-2-imidazolone | 561 |

TABLE 4-continued

| Ex. | Structure | Name | MS (ES) (M + H)+ |
|---|---|---|---|
| 27 | 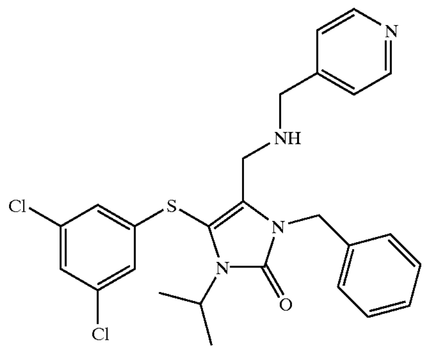 | 1-Benzyl-4-(3,5-dichlorophenylthio)-3-isopropyl-5-{[(pyridin-4-ylmethyl)amino]methyl}-1,3-dihydro-2-imidazolone | 513 |
| 28 | 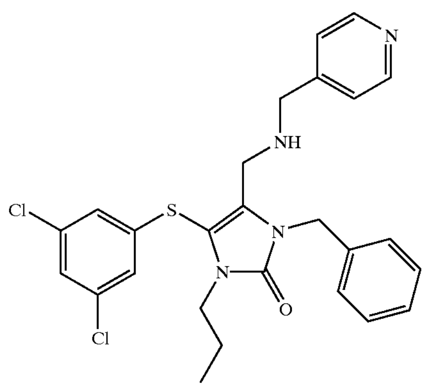 | 1-Benzyl-4-(3,5-dichlorophenylthio)-3-propyl-5-{[(pyridin-4-ylmethyl)amino]methyl}-1,3-dihydro-2-imidazolone | 513 |
| 29 | 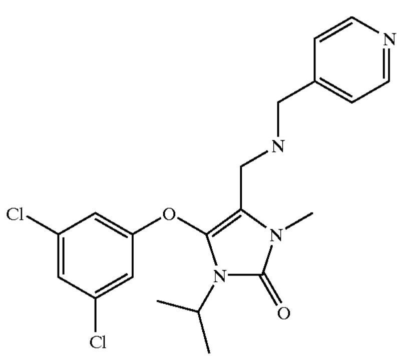 | 4-(3,5-Dichlorophenoxy)-3-isopropyl-1-methyl-5-{[(pyridin-4-ylmethyl)amino]methyl}-1,3-dihydro-2-imidazolone | 421 |
| 30 | 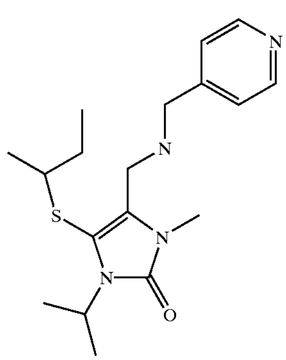 | 4-sec-Butylthio-3-isopropyl-1-methyl-5-{[(pyridin-4-ylmethyl)amino]methyl}-1,3-dihydro-2-imidazolone | 349 |

TABLE 4-continued

| Ex. | Structure | Name | MS (ES) (M + H)+ |
|---|---|---|---|
| 31 | 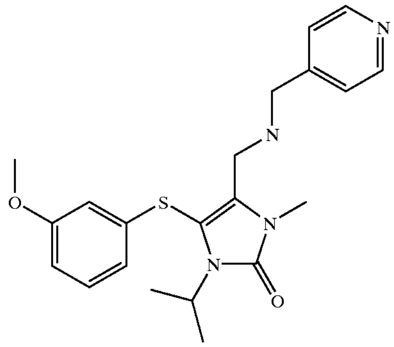 | 1-Isopropyl-5-(3-methoxyphenylthio)-3-methyl-4-{[[(pyridin-4-ylmethyl)amino]methyl}-1,3-dihydro-2-imidazolone | 399 |

EXAMPLE 32

4-(3,5-Dichlorophenylthio)-3-isopropyl-1-methyl-5-(2-phenylethyl-1,3-dihydro-2-imidazolone A solution of 50 mg of 4-(3,5-dichlorophenylthio)-5-styryl-3-isopropyl-1-methyl-1,3-dihydro-2-imidazolone was hydrogenated over a catalytic amount of 5% Pd on carbon for 4 h. The reaction mixture was filtered and evaporated then purified by flash chromatography eluting with 3:1 hexane/ethyl acetate to give 5 mg of a colourless oil. Mass spectrum (ES) m/z 421 [M+H]⁺.

The starting material was prepared as follows:

Intermediate 32A

4-(3,5-Dichlorophenylthio)-5-styryl-3-isopropyl-1-methyl-1,3-dihydro-2-imidazolone Polymer supported triphenylphosphine (1 g, 3 mmol) and 713 μL of benzyl bromide were refluxed in 20 ml of toluene for 3 h. The mixture was allowed to cool to rt and the toluene decanted. The resulting salt was stirred in 10 ml of tetrahydrofuran at 0° C. and treated with potassium tert.-butoxide. This mixture was stirred for 30 min at 0° C. then 345 mg of 5-(3,5-dichlorophenylthio)-2,3-dihydro-1-isopropyl-3-methyl-2-oxo-1H-imidazole-4-carboxaldehyde was added. The mixture was stirred at rt for 3 s then filtered and evaporated. The residue was purified by flash chromatography eluting with 3:2 hexane/ethyl acetate to give 140 mg of a colourless oil. Mass spectrum (ES) m/z 419 [M+H]⁺.

EXAMPLES 49–52

The compounds shown in table 5 were prepared in a manner analogous to that described for examples 13 to 14:

TABLE 5

| Ex. | Structure | Name | MS (ES) (M + H)+ |
|---|---|---|---|
| 49 | 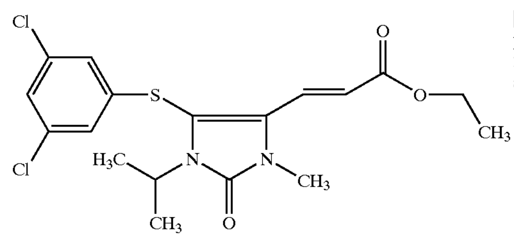 | [E]-3-[5-(3,5-Dichloro-phenylsulfanyl)-1-isopropyl-3-methyl-2-oxo-2,3-dihydro-1H-imidazol-4-yl]-acrylic acid ethyl ester | 416 |
| 50 | 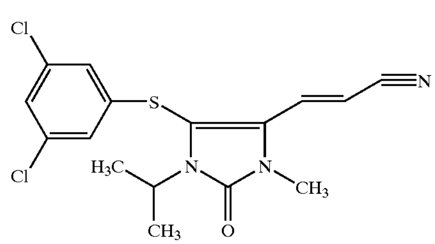 | 3-[5-(3,5-Dichloro-phenylsulfanyl)-1-isopropyl-3-methyl-2-oxo-2,3-dihydro-1H-imidazol-4-yl]-acrylonitrile | 369 |

TABLE 5-continued

| Ex. | Structure | Name | MS (ES) (M + H)+ |
|---|---|---|---|
| 51 | 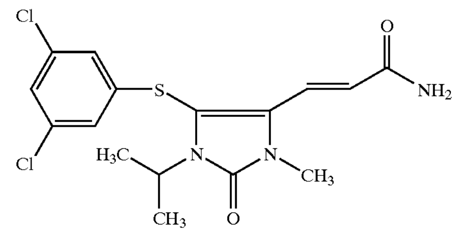 | 3-[5-(3,5-Dichloro-phenylsulfanyl)-1-isopropyl-3-methyl-2-oxo-2,3-dihydro-1H-imidazol-4-yl]-acrylamide | 387 |
| 52 | 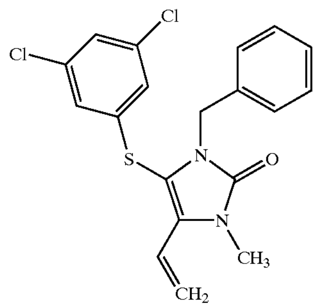 | 1-Benzyl-5-(3,5-dichloro-phenylsulfanyl)-3-methyl-4-vinyl-1,3-dihydro-imidazol-2-one | 392 |

EXAMPLE 53

4-(3,5-Dichloro-phenylsulfanyl)-3-isopropyl-1-methyl-5-pyridin-4-ylmethyl-1,3-dihydro-imidazol-2-one A solution of 160 mg of phosphorus tetraiodide in 15 mL of toluene was heated in the dark at 80° C. for 20 min. To this solution was added dropwise a solution of 150 mg of 4-(3,5-dichloro-phenylsulfanyl)-3-isopropyl-1-methyl-5-[1-hydroxy-1-pyridin-4-ylmethyl]-1,3-dihydro-imidazol-2-one in 5 mL of toluene. The mixture was then heated at 80° C. for 1 h then allowed to cool to room temperature. Then 8 mL of 10% aqueous sodium bisulphite solution was added and the biphasic mixture stirred for 1 h. The aqueous phase was extracted three times with 30 mL of ethyl acetate and combined extracts were washed with brine, dried, filtered and evaporated to give a yellow residue which was purified by flash chromatography on silica gel using ethyl acetate/methanol (19:1) for the elution to give 50 mg as a pale yellow oil. Mass spectrum (ES) m/z 408 [M+H]+.

The starting material 4-(3,5-dichloro-phenylsulfanyl)-3-isopropyl-1-methyl-5-[1-hydroxy-1-pyridin-4-ylmethyl]-1, 3-dihydro-imidazol-2-one was prepared as follow 560 mg of 4-Bromopyridine hydrobromide was treated with 15 mL of 5% aqueous sodium hydrogen carbonate and extracted three times with 20 mL of diethyl ether and combined extracts were washed with brine, dried, filtered and evaporated to give a colourless oil which was dissolved in 3 mL of tetrahydrofuran. To this solution, under nitrogen at room temperature, was added 1.45 mL of a 3.0M solution of isopropyl magnesium chloride in diethyl ether. The reaction mixture was stirred at room temperature for 1.5 h then a solution of 1.0 g of 5-(3,5-dichlorophenylthio)-1-isopropyl-3-methyl-1,3-dihydro-2-imidazolone-4-carboxaldehyde in 10 mL of tetrahydrofuran was added. The reaction mixture was stirred at room temperature overnight then 20 mL of water added. The aqueous phase was extracted three times with 10 mL of dichloromethane and combined extracts were washed with brine, dried, filtered and evaporated to give a yellow oil which was purified by flash chromatography on silica gel using ethyl acetate/hexane (2:1 then 4:1) for the elution to give 250 mg of a pale yellow solid. Mass spectrum (ES) m/z 424 [M+H]+.

What is claimed is:
1. A compound of the formula

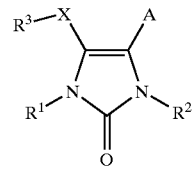

I wherein
R$^1$ is hydrogen, alkyl, cycloalkyl, aryl or alkyl substituted with optionally substituted phenyl;
R$^2$ is hydrogen, alkenyl, alkyl or alkyl substituted with optionally substituted phenyl;
R$^3$ is alkyl, cycloalkyl, optionally substituted phenyl, optionally substituted benzyl or heterocyclyl;
A is alkyl, hydroxy-alkyl, alkenyl, substituted alkenyl, aryl-CH(OH)—, substituted alkyl, or
A is a group of formula Z—CH$_2$—Y—CH$_2$—, wherein
Y is O or NR wherein R is hydrogen or alkyl and
Z is heterocyclyl or optionally substituted aryl;
X is S or O;
with the proviso that (i) only one of R$^1$ and R$^2$ is hydrogen; (ii) when X is O, then R$^1$ cannot be aryl; is hydrogen;
or the pharmaceutically acceptable hydrolyzable esters or the pharmaceutically acceptable salts thereof.

2. The compound according to claim 1 wherein
R$^1$ is hydrogen, C$_{1-12}$-alkyl, C$_{3-8}$-cycloalkyl, aryl or C$_{1-4}$-alkyl substituted with phenyl optionally substituted with 1–5 substituents selected from $C_{1-4}$-alkyl, $C_{1-4}$-alkoxy, hydroxy, fluorine, chlorine and bromine;

$R^2$ is hydrogen, $C_{2-4}$-alkenyl, $C_{1-12}$-alkyl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine;

$R^3$ is $C_{1-12}$-alkyl, $C_{3-8}$-cycloalkyl, phenyl, benzyl or heterocyclyl wherein the phenyl ring of the phenyl and benzyl is optionally substituted with 1–5 substituents selected from $C_{1-4}$-alkyl, $C_{1-4}$-alkoxy, hydroxy, fluorine, chlorine, bromine and cyano;

A is $C_{1-12}$-alkyl, hydroxy-$C_{1-4}$-alkyl, $C_{2-4}$-alkenyl, substituted $C_{2-4}$-alkenyl, aryl-CH(OH)—, $C_{1-4}$-alkyl substituted with $C_{1-4}$-alkoxy, $C_{1-4}$-alkyl-carbonyl-oxy-, heterocyclyl-oxy or A is $C_{1-4}$-alkyl substituted with phenyl optionally substituted with 1–5 substituents or with heterocyclyl optionally substituted with 1–4 substituents wherein the phenyl and heterocyclyl substituents are selected from $C_{1-4}$-alkyl, $C_{1-4}$-alkoxy, hydroxy, fluorine, chlorine and bromine,
wherein substituted $C_{2-4}$-alkenyl is substituted with 1–2 substituents selected from cyano, aminocarbonyl and $C_{1-4}$-alkyl-oxy-carbonyl, or A is a group of formula Z—CH$_2$—Y—CH$_2$—,
wherein
Y is O or NR wherein R is hydrogen or $C_{1-4}$-alkyl and
Z is heterocyclyl or optionally substituted aryl with 1–3 benzyl-oxy groups;

X is S or O;

with the proviso that (i) only one of $R^1$ and $R^2$ is hydrogen; (ii) when X is O, then $R^1$ cannot be aryl.

3. The compound according to claim 1 wherein
$R^1$ is $C_{1-12}$-alkyl, aryl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine;

$R^2$ is $C_{2-4}$-alkenyl, $C_{1-12}$-alkyl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine;

$R^3$ is $C_{1-12}$-alkyl, $C_{3-8}$-cycloalkyl, phenyl, benzyl or heterocyclyl,
wherein a phenyl ring is optionally substituted with 1–5 substituents selected from $C_{1-4}$-alkyl, $C_{1-4}$-alkoxy, hydroxy, fluorine, chlorine, bromine and cyano;

A is $C_{1-7}$-alkyl, hydroxy-$C_{1-4}$-alkyl, $C_{2-4}$-alkenyl, substituted $C_{2-4}$-alkenyl, aryl-CH(OH)—, $C_{1-4}$-alkyl substituted with $C_{1-4}$-alkoxy, $C_{1-4}$-alkyl-carbonyl-oxy-, heterocyclyl-oxy or A is $C_{1-4}$-alkyl substituted with phenyl optionally substituted with 1–5 substituents or with heterocyclyl optionally substituted with 1–4 substituents wherein the phenyl and heterocyclyl substituents are selected from $C_{1-4}$-alkyl, $C_{1-4}$-alkoxy, hydroxy, fluorine, chlorine and bromine,
wherein substituted $C_{2-4}$-alkenyl is substituted with 1–2 substituents selected from cyano, aminocarbonyl and $C_{1-4}$-alkyl-oxy-carbonyl, or A is a group of formula Z—CH$_2$—Y—CH$_2$—,
wherein
Y is O or NR wherein R is hydrogen or $C_{1-4}$-alkyl and
Z is heterocyclyl or optionally substituted aryl with 1–3 benzyl-oxy groups;

X is S or O.

4. The compound according to claim 1 wherein
$R^1$ is $C_{1-7}$-alkyl, phenyl or $C_{1-4}$-alkyl substituted with phenyl;

$R^2$ is $C_{2-4}$-alkenyl, $C_{1-7}$-alkyl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine;

$R^3$ is $C_{1-7}$-alkyl, $C_{3-6}$-cycloalkyl, phenyl, benzyl or heterocyclyl wherein the phenyl ring of the phenyl and benzyl is optionally substituted with 1–5 substituents selected from $C_{1-4}$-alkyl, $C_{1-4}$-alkoxy, hydroxy, fluorine, chlorine, bromine and cyano;

A is $C_{1-7}$-alkyl, hydroxy-$C_{1-4}$-alkyl, $C_{2-4}$-alkenyl, substituted $C_{2-4}$-alkenyl, phenyl-CH(OH)—, $C_{1-4}$-alkyl substituted with $C_{1-4}$-alkoxy, $C_{1-4}$-alkyl-carbonyl-oxy-, heterocyclyl-oxy or A is $C_{1-4}$-alkyl substituted with phenyl optionally substituted with 1–5 substituents or with pyridyl optionally substituted with 1–4 substituents wherein the phenyl and pyridyl substituents are selected from $C_{1-4}$-alkyl, $C_{1-4}$-alkoxy, hydroxy, fluorine, chlorine and bromine,
wherein substituted $C_{2-4}$-alkenyl is substituted with 1–2 substituents selected from cyano, aminocarbonyl and $C_{1-4}$-alkyl-oxy-carbonyl, or A is a group of formula Z—CH$_2$—Y—CH$_2$—,
wherein
Y is O or NR wherein R is hydrogen or $C_{1-4}$-alkyl and
Z is pyridyl or optionally substituted phenyl with 1–3 benzyl-oxy groups;

X is S or O.

5. The compound according to claim 1 wherein
$R^1$ is $C_{1-7}$-alkyl or $C_{1-4}$-alkyl substituted with phenyl;

$R^2$ is $C_{2-4}$-alkenyl, $C_{1-7}$-alkyl or $C_{1-4}$-alkyl substituted with phenyl;

$R^3$ is $C_{1-4}$-alkyl, $C_{3-6}$-cycloalkyl or optionally substituted phenyl,
wherein phenyl is optionally substituted with 1–5 substituents selected from $C_{1-4}$-alkyl, $C_{1-4}$-alkoxy, hydroxy, fluorine, chlorine, bromine and cyano;

A is $C_{1-7}$-alkyl, $C_{2-4}$-alkenyl, substituted $C_{2-4}$-alkenyl, $C_{1-4}$-alkyl substituted with phenyl optionally substituted with 1–5 substituents or with pyridyl optionally substituted with 1–4 substituents wherein the phenyl and pyridyl substituents are selected from $C_{1-4}$-alkyl, $C_{14}$-alkoxy, hydroxy, fluorine, chlorine and bromine,
wherein substituted $C_{2-4}$-alkenyl is substituted with 1–2 substituents selected from cyano, aminocarbonyl and $C_{14}$-alkyl-oxy-carbonyl, or A is a group of formula Z—CH$_2$—Y—CH$_2$—,
wherein
Y is O or NR wherein R is hydrogen or $C_{14}$-alkyl and
Z is pyridyl or optionally substituted phenyl with 1–3 benzyl-oxy groups;

X is S or O.

6. The compound according to claim 1 wherein
$R^1$ is $C_{1-7}$-alkyl;
$R^2$ is $C_{1-7}$-alkyl;
$R^3$ is phenyl optionally substituted with 1–5 substituents selected from $C_{14}$-alkyl, $C_{14}$-alkoxy, hydroxy, fluorine, chlorine, bromine and cyano;

A is $C_{1-4}$-alkyl substituted with phenyl optionally substituted with 1–3 substituents or with pyridyl optionally substituted with 1–2 substituents wherein the phenyl and pyridyl substituents are selected from $C_{1-4}$-alkyl, $C_{1-4}$-alkoxy, hydroxy, fluorine, chlorine and bromine, or A is a group of formula Z—CH$_2$—Y—CH$_2$—, wherein
Y is O or NR wherein R is hydrogen or $C_{1-4}$-alkyl and
Z is pyridyl or phenyl;
X is S or O.
7. The compound according to claim 1 wherein
$R^1$ is $C_{1-4}$-alkyl;
R is $C_{1-4}$-alkyl;
$R^3$ is phenyl optionally substituted with 1–3 substituents selected from $C_{1-2}$-alkyl, $C_{1-2}$-alkoxy, hydroxy, fluorine, chlorine, bromine and cyano;
A is $C_{1-2}$-alkyl substituted with phenyl optionally substituted with 1–3 substituents or with pyridyl optionally substituted with 1–2 substituents wherein the phenyl and pyridyl substituents are selected from $C_{1-4}$-alkyl, $C_{1-4}$-alkoxy, hydroxy, fluorine, chlorine and bromine, or
A is a group of formula Z—CH$_2$—Y—CH$_2$—,
wherein
Y is O or NR wherein R is hydrogen or $C_{1-2}$-alkyl and
Z is pyridyl or phenyl;
X is S or O.
8. The compound according to claim 1 wherein
$R^1$ is isopropyl;
$R^2$ is methyl or ethyl;
$R^3$ is phenyl optionally substituted with 1–3 chlorine substituents;
A is $C_{1-2}$-alkyl substituted with phenyl or pyridyl, or
A is a group of formula Z—CH$_2$—Y—CH$_2$—,
wherein
Y is O or NR wherein R is hydrogen or $C_{1-2}$-alkyl and
Z is pyridyl or phenyl;
X is S or O.
9. The compound according to claim 1 wherein
$R^1$ is isopropyl;
$R^2$ is methyl;
$R^3$ is optionally substituted phenyl,
wherein phenyl may be substituted with 1–2 chlorine substituents;
A is $C_{1-2}$-alkyl substituted with pyridyl, or
A is a group of formula Z—CH$_2$—Y—CH$_2$—,
wherein
Y is O or NR wherein R is hydrogen or $C_{1-2}$-alkyl and
Z is pyridyl;
X is S or O.
10. A compound of the formula

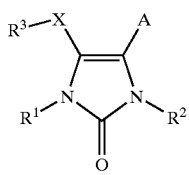

I wherein
$R^1$ is hydrogen, $C_{1-12}$-alkyl, $C_{3-8}$-cycloalkyl, aryl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine;
$R^2$ is hydrogen, $C_{1-12}$-alkyl or $C_{1-4}$-alkyl substituted with phenyl optionally substituted with 1–5 substituents selected from $C_{1-4}$-alkyl, $C_{1-4}$-alkoxy, hydroxy, fluorine, chlorine and bromine;
$R^3$ is $C_{1-12}$-alkyl, $C_{3-8}$-cycloalkyl, phenyl or benzyl, wherein the phenyl ring of the phenyl and benzyl is optionally substituted with 1–5 substituents selected from $C_{1-4}$-alkyl, $C_{1-4}$-alkoxy, hydroxy, fluorine, chlorine and bromine;
A is hydroxy-$C_{1-4}$-alkyl or aryl-CH(OH)—; or
A is a group of formula Z—CH$_2$—Y—CH$_2$—,
wherein
Y is O or NR wherein R is hydrogen or $C_{1-4}$-alkyl and
Z is aryl or heterocyclyl; or
A is $C_{1-4}$-alkyl substituted with phenyl optionally substituted with 1–5 substituents or with heterocyclyl optionally substituted with 1–4 substituents wherein the phenyl and heterocyclyl substituents are selected from $C_{1-4}$-alkyl, $C_{1-4}$-alkoxy, hydroxy, fluorine, chlorine and bromine;
X is S or O;
with the proviso that (i) only one of $R^1$ and $R^2$ is hydrogen; (ii) when X is O, then $R^1$ cannot be aryl;
or the pharmaceutically acceptable hydrolyzable esters or the pharmaceutically acceptable salts thereof.
11. The compound according to claim 1 which is selected from the group consisting of:
4-(3,5-dichlorophenylthio)-5-hydroxymethyl-3-isopropyl-1-methyl-1,3-dihydro-2-imidazolone,
5-(benzylaminomethyl)-4-(3,5-dichlorophenylthio)-3-isopropyl-1-methyl-1,3-dihydro-2-imidazolone,
4-(3,5-dichlorophenylthio)-5-(alpha(RS)-hydroxybenzyl)-3-isopropyl-1-methyl-1,3-dihydro-2-imidazolone,
4-(3,5-dichlorophenylthio)-5-hydroxymethyl-1-methyl-3-phenyl-1,3-dihydro-2-imidazolone,
5-benzyloxymethyl-4-(3,5-dichlorophenylthio)-3-isopropyl-1-methyl-1,3-dihydro-2-imidazolone,
4-(3,5-dichlorophenylthio)-3-isopropyl-1-methyl-5-{[(pyridin-4-ylmethyl)amino]methyl}-1,3-dihydro-2-imidazolone,
5-(benzylamino-methyl)-3-isopropyl-1-methyl-4-phenylthio-1,3-dihydro-2-imidazolone,
3-isopropyl-1-methyl-4-phenylthio-5-{[(pyridin-4-ylmethyl)amino]methyl}-1,3-dihydro-2-imidazolone,
5-benzyloxymethyl-4-(3,5-dichlorophenoxy)-3-isopropyl-1-methyl-1,3-dihydro-2-imidazolone,
5-benzyloxymethyl-4-(3,5-dichlorophenylthio)-1-methyl-3-phenyl-1,3-dihydro-2-imidazolone,
4-(3,5-dichlorothio)-3-isopropyl-1-methyl-5-(pyridin-4-ylmethoxymethyl)-1,3-dihydro-2-imidazolone,
5-(benzylaminomethyl)-4-(3,5-dimethylphenylthio)-3-isopropyl-1-methyl-1,3-dihydro-2-imidazolone,
4-cyclohexylthio-3-isopropyl-1-methyl-5-{[(pyridin-4-ylmethyl)amino]methyl}-1,3-dihydro-2-imidazolone,
4-(3,5-dimethylphenythio)-3-isopropyl-1-methyl-5-{[(pyridin-4-ylmethyl)amino]methyl}-1,3-dihydro-2-imidazolone,
4-benzylthio-3-isopropyl-1-methyl-5-{[(pyridin-4-ylmethyl)-amino]-methyl}-1,3-dihydro-2-imidazolone,
4-(3-chlorophenylthio)-3-isopropyl-1-methyl-5-{[(pyridin-4-ylmethyl)amino]methyl}-1,3-dihydro-2-imidazolone,
3-isopropyl-4-isopropylthio-1-methyl-5-{[(pyridin-4-ylmethyl)amino]methyl}-1,3-dihydro-2-imidazolone,
4-isobutylthio-3-isopropyl-1-methyl-5-{[(pyridin-4-ylmethyl)amino]methyl}-1,3-dihydro-2-imidazolone,
4-(3,5-dichlorophenylthio)-3-isopropyl-1-(4-methoxybenzyl)-5-{[(pyridin-4-ylmethyl)amino]methyl}-1,3-dihydro-2-imidazolone,
4-(3,5-dichlorophenylthio)-5-hydroxymethyl-3-isopropyl-1-(4-methoxybenzyl)-1,3-dihydro-2-imidazolone, 4-(3,5-dichlorophenylthio)-3-isopropyl-1-methyl-5-phenethyl-1,3-dihydro-2-imidazolone,
4-(3,5-dichlorophenylthio)-5-(2-hydroxybenzyl)-3-isopropyl-1-methyl-1,3-dihydro-2-imidazolone,
3-benzyl-4-(3,5-dichlorophenylthio)-1-methyl-5-{[(pyridin-4-ylmethyl)amino]methyl}-1,3-dihydro-2-imidazolone,
1,3-dibenzyl-4-(3,5-dichlorophenylthio)-5-{[(pyridin-4-ylmethyl)amino]methyl}-1,3-dihydro-2-imidazolone,
1-benzyl-4-(3,5-dichlorophenylthio)-3-isopropyl-5-{[(pyridin-4-ylmethyl)amino]methyl}-1,3-dihydro-2-imidazolone,
1-benzyl-4-(3,5-dichlorophenylthio)-3-propyl-5-{[(pyridin-4-ylmethyl)amino]methyl}-1,3-dihydro-2-imidazolone,
5-benzyl-4-(3,5-dichlorophenylthio)-3-isopropyl-1-methyl-1,3-dihydro-2-imidazolone,
3-benzyl-4-(3,5-dichlorophenylthio)-5-hydroxymethyl-1-methyl-1,3-dihydro-2-imidazolone,
4-(3,5-dichlorophenoxy)-3-isopropyl-1-methyl-5-{[(pyridin-4-ylmethyl)amino]methyl}-dihydro-2-imidazolone,
4-sec-butylthio-3-isopropyl-1-methyl-5-{[(pyridin-4-ylmethyl)amino]methyl}-1,3-dihydro-2-imidazolone,
3-isopropyl-4-(3-methoxyphenylthio)-1-methyl-5-{[(pyridin-4-ylmethyl)amino]methyl}-1,3-dihydro-2-imidazolone, and
3-benzyl-4-(3,5-dichlorophenylthio)-5-(1-hydroxyethyl)-1-methyl-1,3-dihydro-2-imidazolone.

12. The compound according to claim 1 is selected from the group consisting of:
4-(3,5-Dichloro-phenylsulfanyl)-3-isopropyl-5-methoxymethyl-1-methyl-1,3-dihydro-imidazol-2-one,
4-Hydroxymethyl-3-methyl-1-phenyl-5-(pyridin-4-ylsulfanyl)-1,3-dihydro-imidazol-2-one,
1-Benzyl-4-hydroxymethyl-3-methyl-5-(pyridin-4-ylsulfanyl)-1,3-dihydro-imidazol-2-one; hydrochloric acid,
4-(3,5-Dichloro-phenylsulfanyl)-3-isopropyl-1-methyl-5-(pyridin-3-ylmethoxymethyl)-1,3-dihydro-imidazol-2-one,
4-(4-Benzyloxy-benzyloxymethyl)-5-(3,5-dichloro-phenylsulfanyl)-1-isopropyl-3-methyl-1,3-dihydro-imidazol-2-one,
Acetic acid 5-(3,5-dichloro-phenylsulfanyl)-1-isopropyl-3-methyl-2-oxo-2,3-dihydro-1H-imidazol-4-ylmethyl ester,
4-(3,5-Dichloro-phenylsulfanyl)-3-isopropyl-1-methyl-5-(pyridin-4-yloxymethyl)-1,3-dihydro-imidazol-2-one,
3-(5-Benzyl-3-isopropyl-1-methyl-2-oxo-2,3-dihydro-1H-imidazol-4-ylsulfanyl)-benzonitrile,
4-Benzyl-5-isobutylsulfanyl-1-isopropyl-3-methyl-1,3-dihydro-imidazol-2-one,
4-Benzyl-1-isopropyl-5-isopropylsulfanyl-3-methyl-1,3-dihydro-imidazol-2-one,
4-Benzyl-1-isopropyl-3-methyl-5-methylsulfanyl-1,3-dihydro-imidazol-2-one,
4-(3,5-Dichloro-phenylsulfanyl)-5-isobutyl-3-isopropyl-1-methyl-1,3-dihydro-imidazol-2-one,
4-Benzyl-5-(3,5-dichloro-phenylsulfanyl)-3-ethyl-1-isopropyl-1,3-dihydro-imidazol-2-one,
1-Allyl-5-benzyl-4-(3,5-dichloro-phenylsulfanyl)-3-isopropyl-1,3-dihydro-imidazol-2-one,
4-(3,5-Dichloro-phenylsulfanyl)-1-ethyl-3-isopropyl-5-pyridin-4-ylmethyl-1,3-dihydro-imidazol-2-one,
1-Allyl-4-(3,5-dichloro-phenylsulfanyl)-3-isopropyl-5-pyridin-4-ylmethyl-1,3-dihydro-imidazol-2-one,
[E]-3-[5-(3,5-Dichloro-phenylsulfanyl)-1-isopropyl-3-methyl-2-oxo-2,3-dihydro-1H-imidazol-4-yl]-acrylic acid ethyl ester,
3-[5-(3,5-Dichloro-phenylsulfanyl)-1-isopropyl-3-methyl-2-oxo-2,3-dihydro-1H-imidazol-4-yl]-acrylonitrile,
3-[5-(3,5-Dichloro-phenylsulfanyl)-1-isopropyl-3-methyl-2-oxo-2,3-dihydro-1H-imidazol-4-yl]-acrylamide,
1-Benzyl-5-(3,5-dichloro-phenylsulfanyl)-3-methyl-4-vinyl-1,3-dihydro-imidazol-2-one, and
4-(3,5-Dichloro-phenylsulfanyl)-3-isopropyl-1-methyl-5-pyridin-4-ylmethyl-1,3-dihydro-imidazol-2-one.

13. A compound of the formula

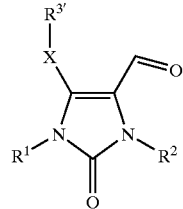

wherein
R$^1$ is hydrogen, alkyl, cycloalkyl, aryl or alkyl substituted with optionally substituted phenyl;
R$^2$ is hydrogen, alkenyl, alkyl or alkyl substituted with optionally substituted phenyl;
R$^{3'}$ is C$_{7-12}$-alkyl, C$_{3-8}$-cycloalkyl, phenyl or benzyl wherein the phenyl ring of the phenyl or benzyl is optionally substituted with 1–5 substituents selected from C$_{1-4}$-alkyl, C$_{1-4}$-alkoxy, hydroxy, fluorine, chlorine or bromine, and
X is S or O.

14. A method for the treatment of HIV infection comprising administering a therapeutically effective amount of a compound of the formula

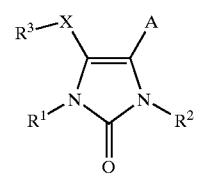

wherein
R$^1$ is hydrogen, alkyl, cycloalkyl, aryl or alkyl substituted with optionally substituted phenyl;
R$^2$ is hydrogen, alkenyl, alkyl or alkyl substituted with optionally substituted phenyl;
R$^3$ is alkyl, cycloalkyl, optionally substituted phenyl, optionally substituted benzyl or heterocyclyl;
A is alkyl, hydroxy-alkyl, alkenyl, substituted alkenyl, aryl-CH(OH)—, substituted alkyl, or
A is a group of formula Z—CH$_2$—Y—CH$_2$—,
 wherein
 Y is O or NR wherein R is hydrogen or alkyl and
 Z is heterocyclyl or optionally substituted aryl;
X is S or O;
with the proviso that (i) only one of R$^1$ and R$^2$ is hydrogen; (ii) when X is O, then R$^1$ cannot be aryl;
or the pharmaceutically acceptable hydrolyzable esters or the pharmaceutically acceptable salts thereof.

* * * * *

UNITED STATES PATENT AND TRADEMARK OFFICE
CERTIFICATE OF CORRECTION

PATENT NO. : 6,518,293 B2
DATED : February 11, 2003
INVENTOR(S) : Dymock et al.

It is certified that error appears in the above-identified patent and that said Letters Patent is hereby corrected as shown below:

Column 81,
Line 58, delete "C14-alkyl, C14-alkoxy" and insert -- C1-4 alkyl, C1-4 alkoxy --

Signed and Sealed this

Twelfth Day of August, 2003

JAMES E. ROGAN
*Director of the United States Patent and Trademark Office*